(12) United States Patent
Gunn et al.

(10) Patent No.: US 6,586,172 B1
(45) Date of Patent: Jul. 1, 2003

(54) DEVICE FOR TREATMENT OF BIOLOGICAL FLUIDS

(75) Inventors: Andrew Gunn, Angus (GB); Ian David Cameron, Dundee (GB); Duncan Stephen Pepper, Edinburgh (GB); Shirley Lynn MacDonald, Galashiels (GB); Qiangyi Li, Edinburgh (GB)

(73) Assignee: Iatros Limited (GB)

( * ) Notice: Subject to any disclaimer, the term of this patent is extended or adjusted under 35 U.S.C. 154(b) by 0 days.

(21) Appl. No.: 09/806,616

(22) PCT Filed: Oct. 4, 1999

(86) PCT No.: PCT/GB99/03082

§ 371 (c)(1), (2), (4) Date: Mar. 30, 2001

(87) PCT Pub. No.: WO00/20045

PCT Pub. Date: Apr. 13, 2000

(30) Foreign Application Priority Data

Oct. 2, 1998 (GB) .............................................. 9821342

(51) Int. Cl.⁷ ................................................. A01N 1/02
(52) U.S. Cl. .......................... 435/2; 422/24; 422/186.3; 356/426; 356/427
(58) Field of Search ................................ 435/2; 422/24, 422/186.3; 356/426, 427

(56) References Cited

FOREIGN PATENT DOCUMENTS

| GB | 2 200 020 B | 6/1991 |
|---|---|---|
| WO | WO 94/28210 | 12/1994 |
| WO | WO 95/32732 | 12/1995 |

OTHER PUBLICATIONS

Conacher, J., *The Use of Ultra Violet Light for Water Disinfection*, The Brewer, pp. 3–8 (May 1986).

*Primary Examiner*—Leon B. Lankford, Jr.
(74) *Attorney, Agent, or Firm*—Myers Bigel Sibley & Sajovec

(57) ABSTRACT

The present invention relates to a method and apparatus for effective inactivation of micro-organisms in fluids with relatively high absorbance so as to limit damage. The apparatus has a large diameter passage (2) flow-through UV radiation system with a static mixer system (11) providing an intensive fluid flow mixing within an irradiation area in which the fluid flow is controlled to provide a flow rate not less than a minimum flow rate corresponding to a maximum fluid residence time within said irradiation area required for efficient mixing, and a maximum flow rate providing a minimum residence time for effective inactivation.

23 Claims, 7 Drawing Sheets

DEVICE FOR TREATMENT OF BIOLOGICAL FLUIDS

CROSS-REFERENCE TO RELATED APPLICATIONS

The present application is a national phase filing based on PCT International Application No. PCT/GB99/03082 filed Oct. 4, 1999. This PCT application claims priority to Great Britain Application No. 9821342.4 filed Oct. 2, 1998. The above PCT application was published in the English language as WO 00/20045.

The present invention relates a method of and a device for the UV-irradiation of a biological fluid of high optical density such as those encountered in beverage industries including dairy, distilling and brewing, and water treatment industries including sewerage and purification and, especially to the inactivation micro-organisms and lymphocytes and the like, including viruses, moulds, yeasts and other similar organisms which may be found in human or non-human blood and products derived from blood, as well as various other body fluids such as, for example, milk from transgenic animals, and synthetic fluids manufactured for use as replacements for any such body fluids or components thereof.

Conventionally inactivation of lymphocytes in biological fluids is effected by administration of immune-suppressive drugs to the patient. However this procedure involves serious risks to the patient due to the various adverse and often severe side effects of such drugs. Whilst various procedures for extracorporeal treatment of blood have been previously proposed these do not produce complete inactivation of the lymphocyte population and/or employ apparatus which is relatively cumbersome, expensive and/or impractical to operate.

In the case of contaminating microorganisms such as bacteria and viruses, various treatments have been proposed including for example, extended incubation at high temperatures and microwave irradiation. These treatments are quite often slow (several hours to even days) and generally require relatively expensive apparatus as well as stringent safety precautions to be followed by the operators of the equipment.

It has been found by others that a combination of UV irradiation with the use of chemical additives for example a photosensitiser such as furocoumarins, which may be used to increase the effectiveness (represented as $\log_{10}$ kill) of the irradiation process. Typical examples of processes of this type can be found in WO94/28120 (MARGOLIS-NUNNO) and WO95/32732 (PARKKINEN).

The addition of photosensitive chemicals such as furocoumarins to the biological fluid has been proposed in order to effect more efficient transfer of energy from the UV radiation source to the target micro-organisms, thereby killing or inactivating the micro-organism without the need for excessive dosages of radiation which can be damaging to the components of the biological fluid. In more detail microorganisms, viral and other contaminants of biological fluids can be photo-dynamically inactivated by the addition of photo-sensitisers to the fluid, which can then be irradiated. The photo-sensitiser can transfer the energy gain from the irradiation to the microorganism by means of, for example, an electron transfer reaction. A second mode of inactivation by photosensitive compounds (most commonly in the presence of nucleic acids) is where the photosensitive compound upon irradiation reacts with nucleic acid residues, typically guanine in DNA. This reaction inactivates the nucleic acid residue and therefore inactivates the microorganism.

The addition of chemicals to the biological fluid has, though, the disadvantage that the chemical and/or its breakdown product(s) are still present within the biological fluid after irradiation. This is generally undesirable in that the chemicals and/or their breakdown products are a source of contamination of the biological fluid. Additionally, the chemicals themselves can be relatively expensive and require the extra step of adding them to the biological fluid, which can be time consuming, and thereby costly in man hours and also introduces a potential source of error in efficient treatment of the biological fluid. To remove or inactivate the chemicals and/or their breakdown products it is necessary to provide one or more further steps in the treatment method and the apparatus thereof for treating the biological fluid, which has obvious cost implications.

The exposure of a biological fluid to UV irradiation can result in damage to various components of the biological fluid, for example enzymes and other functional proteins. Therefore, the UV irradiation source should not be too powerful nor may the fluid be exposed to said UV radiation for too long, if one is to avoid damaging the components of fluid.

To ensure that substantially all of the fluid receives a sufficient dose of radiation, it has been found that intensive mixing of the fluid to be treated during irradiation increases the efficiency of the irradiation process. A device provided with a highly efficient mixer is described in the Applicant's patent GB 2,200,020B. The device of GB 2,200,020B describes a device which inter alia has a static flow mixing means which in use of the device repeatedly divides and mixes the biological fluid as it is irradiated. The principal device of GB 2,200,020B has a plurality of narrow bore ($\leq 2$ mm) passageways (see page 5, lines 16 to 19) through which biological fluid flows in use of the device. These narrow passageways ensure that the biological fluid receives an adequate dosage of UV radiation by passing the biological fluid close (i.e. at a distance of less than 1 mm) to UV transparent walls of the device. The biological fluid must pass close to the walls because of the relatively high absorption of UV radiation by many biological fluids, especially fluids with high OD such as blood as well as fluids which are substantially transparent but nevertheless have quite high OD, such as, for example, Human Serum Albumin (HSA) which has $OD_{280}$ of 24.5, plasma which typically has $OD_{280}$ of 50 to 60, and various immunogamma globulin (IgG) products which can have $OD_{280}$ values of 200 or more, which means that the radiation hardly penetrates at all into the body of the biological fluid. The intensity of the UV radiation at a given point in the biological fluid is proportional to the inverse square of the distance of the point from the source of the UV radiation. It is for this reason that the biological fluid, in use of the device described in GB 2,200,020B, is passed through narrow bore passageways. One limitation of a device such as the principal device of GB 2,200,020B is that as a result of passing through such narrow passageways, the biological fluid is susceptible to heat damage from the radiation source which heat(s) the walls of the device such that vital components of the biological fluid are damaged, for example proteins, red blood cells, etc. Heat damage is not desirable and is a limiting factor in the use of more powerful radiation sources and their proximity to the fluid to be treated. In order to reduce the heat-damage, the irradiation chamber of the device can be cooled, for example by air-cooling using a fan, as described in Example 1 of GB 2,200,020B. Nevertheless, as a result of the relatively low flow rates (e.g. 130 ml/min to 1200 ml/min), the biological fluid is in contact with or close proximity to the walls of the device for a relatively long time which results in correspondingly greater risk of heat damage.

Yet another problem that arises in this field is that in order to minimise heat damage and damage from excessive irradiation, it is desirable for the treatment time or residence time in the irradiation zone to be minimised. On the other hand if the residence time is too short, then a safe level of virus inactivation or log kill may not be achieved. Inactivation on a commercial scale can, however, involve treatment of relatively large volumes e.g. hundreds or thousands of liters of precious and scarce materials such as albumin, IgG, plasma and the like, and it is extremely expensive and wasteful of such precious and scarce materials to carry out optimisation of the considerable number of various different treatment parameters and conditions for each batch of material to be treated. There is accordingly an important need for providing a means for predicting log kill levels for different fluid batches with different Ods etc. e.g. $OD_{280}$ for plasma can typically range between 45 and 55 and beyond.

It is an object of the present invention to avoid or minimise at least one of the above-mentioned disadvantages by providing method and apparatus for treatment of a biological fluid to kill or inactivate microorganisms and the like.

It has now surprisingly been found that effective killing or inactivation of micro-organisms in fluids with relatively high absorbance—typically with $OD_{280}$ values in the range from 1 to 200, can be effectively controlled in a through-flow system in a way which tends to maximise inactivation and limit damage. More particularly we have found that the rate of microorganism inactivation—so called log kill, can be effectively controlled in such fluids in a relatively large diameter passage flow-through UV radiation system by using a static mixer system formed and arranged so as to provide an intensive fluid flow mixing within an irradiation area in which the fluid flow in said large diameter passage is irradiated with UV radiation of a micro-organism-inactivating wavelength, and controlling the fluid flow rate so as to: provide a flow rate which is not less than a minimum flow rate corresponding to a maximum fluid residence time within said irradiation area required for efficient mixing as indicated by: the maintenance of a substantially close relation between actual log kill and log kill as predicted by the below indicated relationship, with increasing residence time which obtains above said minimum flow rate, or a Reynolds number for said fluid flow of at least 50, preferably at least 100, and to provide a (minimum) desired log kill rate achieved via passage of the fluid flow through the irradiation area with a (minimum) residence time in said irradiation area which residence time is defined in accordance with the following relationship:

$\log_{10}$ kill=$K$×Flux×Residence time×Z/OD×Tube Diameter wherein Flux indicates the amount of UV radiation incident on the passage containing the fluid flow in the irradiation area (immediately inside the passage wall), in mW cm$^{-2}$; OD is the Optical Density of the fluid at said micro-organism inactivating UV radiation wavelength (typically in the range 250 to 280 $\mu$m); K is an empirically derived constant; Tube Diameter is the internal diameter of the vessel in the irradiation area, in cms; and Z is related to certain physical properties of the fluid affecting its flow through the UV radiation passage.

In more detail, $Z=u(\rho/\mu)/Re^m$ wherein u is fluid flow velocity in cm/sec, $\rho$ is fluid density in kg/m$^3$, $\mu$ is fluid viscosity in cp, Re is the Reynolds number of the fluid whose value is defined by the formula Re=du$\rho/\mu$ where d, u, $\rho$ and $\mu$ have the same meaning as before, and m is a characteristic of the static mixer system whose value is determined experimentally. In the case of a static flow mixer device of the kind comprising a multiplicity of alternating rotational sense diametrically offset half-turn helical screw elements as further described hereinbelow, m typically has a value of the order of 0.4.

It will be appreciated that the above relationship can be presented in various different ways, and/or can be simplified to a greater or lesser extent by keeping certain variables constant. Thus, for example, if the UV radiation source (number, arrangement, power, separation, type etc of lamps used) is kept constant then the radiation flux will vary only with the UV (transmission characteristics of the wall defining the passage through which the fluid being treated flows and the "Flux" could be replaced by a relative radiation transmission value Tm for the material of the wall defining the passage, and a constant which may be incorporated into the general constant K of the above general relationship. By way of example, if a silica glass with a given wall thickness is taken to have a transmission of 1.0, then the Tm value for FEP (fluorinated ethylene propylene) plastics of the same wall thickness is 0.83. By extracting the u component from Z and combining it with the Residence time component $t_R$ it is then possible to present the above relation in the following form:

$$\mathrm{Log}_{10}\, kill = \frac{K \cdot Tm(\rho/\mu)L}{OD \cdot d \cdot Re^{0.4}}$$

wherein L is the total effective length of the irradiation area (i.e. actual length×number of passes), and the other symbols have the same meaning as before.

Furthermore it has been found that the above relation may be simplified somewhat for fluids having ODs in the lower part of the range, generally in the range from 1 to 50, especially from 1 to 30. Thus in one aspect it has also been found the effective killing or inactivation of micro-organisms in fluids with relatively high absorbance—typically with $OD_{280}$ values in the range from 1 to 50, can be effectively controlled in a through-flow system in a way which tends to maximise inactivation and limit damage. More particularly we have found that the rate of microorganism inactivation—so called log kill, can be effectively controlled in such fluids in a relatively large diameter passage flow-through UV radiation system by using a static mixer system formed and arranged so as to provide an intensive fluid flow mixing within an irradiation area in which the fluid flow in said large diameter passage is irradiated with UV radiation of a micro-organism-inactivating wavelength, and controlling the fluid flow rate so as to provide a flow rate not less than a minimum flow rate corresponding to a maximum fluid residence time within said irradiation area required for efficient mixing as indicated by the maintenance of a substantially linear relation between log kill and residence time which obtains above said minimum flow rate, and a (minimum) desired log kill rate achieved via passage of the fluid flow through the irradiation area so as to provide a (minimum) residence time in said irradiation area which residence time is defined in accordance with the following relationship:

$\log_{10}$ kill=$K$×Flux×Residence time/OD×Tube Diameter wherein Flux indicates the amount of UV radiation incident on the passage containing the fluid flow in the irradiation area, in mW cm$^{-2}$; OD is the Optical Density of the fluid at said micro-organism inactivating UV radiation wavelength (typically in the range 250 to 280 μm); K is an empirically derived constant; and Tube Diameter is the internal diameter of the vessel in the irradiation area, in cms.

Log$_{10}$ kill or log$_{10}$ Reduction Value (LRV) is taken herein to be a measure of the efficiency of a process used for killing or inactivating micro-organisms, such a process being for example irradiation of a sample containing said micro-organism. For example, if 99.0% of all micro-organisms in a given fluid are killed or inactivated, this is equivalent to log 10$^2$ or 2 log$_{10}$ kill or LRV; and so on. An acceptable efficiency has generally been found to be a 4 to 6 log$_{10}$ kill i.e. when 99.99 to 99.9999% of all micro-organisms in a sample are killed/inactivated. The rate or level of micro-organism kill is generally determined by comparing the initial or starting, and final titres of the micro-organism in the fluid in an assay for the micro-organism (measured by determining the greatest dilution at which the micro-organism can just be detected).

Thus in one aspect the present invention provides an apparatus suitable for use in the UV-irradiation of a biological fluid containing a desired component and a contaminating micro-organism, which apparatus comprises a longitudinally extending vessel having wall means of a UV-transparent material disposable, in use of the apparatus, in close proximity to a UV radiation source within an irradiation area and having an inlet and outlet and a passage means formed and arranged so as to define a flow path extending therebetween which is

- substantially free of substantial discontinuities so as to avoid substantially turbulence in fluid flowing therealong in use of the apparatus, and
- having an irradiation zone adjacent said UV-transparent wall means for receiving UV radiation from said UV radiation source, in use of the apparatus,
- said passage means having a static flow mixing means with a multiplicity of mixer elements for repeatedly subjecting the fluid flow to a mixing operation comprising dividing and re-mixing of the fluid flow, in use of the apparatus, which static flow mixing means extends along said flow path along at least said irradiation zone,
- said vessel having an internal diameter of at least 4 mm, and said apparatus including fluid flow supply means formed and arranged for passing fluid through said vessel, in use of the apparatus,
- so that said fluid flow is subjected to at least 20 said mixing operations,
- at a fluid flow rate not less than a minimum flow rate corresponding to a maximum fluid residence time (within said irradiation area) required for efficient mixing as indicated by the maintenance of a substantially linear relation between log kill and residence time which obtains above said minimum flow rate and at a fluid flow rate not greater than a maximum fluid flow rate corresponding to a minimum residence time in said irradiation area required for effective inactivation of a said contaminating micro-organism by providing a desired log kill of said micro-organism, (preferably not less than that required for a 4 log kill of said contaminating micro-organism, in general not less than 1 second, for example, not less than 10 seconds), and
- not greater than that at which significant degradation of said desired component occurs, preferably not greater than that at which 10% aggregation (desirably not more than about 1%) and/or 20% loss of biological activity of said desired component occurs, wherein said minimum residence time in said irradiation area is defined in accordance with the following relationship:

$$\log_{10} \text{kill} = K \times \text{Flux} \times \text{Residence time}/\text{OD} \times \text{Tube Diameter}$$

wherein Flux indicates the amount of UV radiation incident on the passage containing the fluid flow in the irradiation area, in mW cm$^{-2}$; OD is the Optical Density of the fluid at the wavelength in the region where substantial virus inactivation takes place (typically in the range 250 to 280 μm); K is an empirically derived constant; and Tube Diameter is the internal diameter of the vessel in the irradiation area, in cms, whereby in use of the apparatus substantially the whole of the fluid may be exposed to a similar micro-organism inactivating level of UV-irradiation whilst minimizing damage to the desired component(s) of the fluid.

In another aspect the present invention provides a method of treating a biological fluid having a restricted UV transmissibility with an OD$_{280}$ of from 1 to 200 using an apparatus of the present invention. (For the avoidance of doubt all ODs herein are the OD for a path length of 1 cm unless otherwise indicated).

Thus by means of the present invention it is possible to achieve effective micro-organism inactivation of biological fluids with high optical density whilst minimizing damage to the desired component(s) of the fluid, without the need for using additives or other special measures in order to achieve micro-organism inactivation and/or to protect the desired component(s). It will be appreciated nevertheless that if it is desired, for any reason, to include an additive in the fluid to be treated in an apparatus or method of the present invention and/or use other measures, then this may be done without departing from the scope of the present invention.

There may also be used protective additives to reduce damage such as aggregation and/or loss of biological activity.

Various protective additives are known in the art including inter alia vitamin E for protecting cells against damage as described in WO95/20961; ascorbate to protect against loss of functional activity of plasma constituents such as coagulation factors as described in WO95/32732; and so-called "quenchers" of free radicals and/or active forms of oxygen such as rutin and quercetin and other flavonoids, and other stabilisers such as sugars e.g. mannitol, and amino acids, for reducing loss of functional activity of blood components and/or protecting against cell damage as described in, for example, WO94/28120.

It is a particular advantage of the present invention that it can be used more or less readily in combination with various other known methods for sterilisation of fluids and viral inactivation either before or after, or simultaneously together therewith. Various methods are more or less well known in the art and include inter alia, conventional wet heat treatment or pasteurisation comprising incubation of fluid at an elevated temperature for a given period of time e.g., 60° C. for 10 hours—with or without stabilisers—as generally used for albumin; dry heat treatment comprising incubation of freeze dried fluid components at an elevated temperature for a given period of time e.g., 60 to 100° C. for 10 to 72 hours as generally used for components such as Factor VIII; ultra-filtration; and solvent detergent treatment wherein the fluid is intimately admixed with a solvent detergent system such as 1% tri(n-butyl)phosphate (TNBP) and 1% Triton X-100 or Tween 80 and incubated together therewith for a given period of time e.g. 4 hours at 30° C., followed by removal of the solvent detergent system, conveniently by hydrophobic chromatography. Details of solvent detergent treatments are described in inter alia WO94/28120; and various U.S. patents including inter alia U.S. Pat. Nos. 4,946,648, 4,481,189, and 4,540,573.

One feature of solvent detergent treatment is that it may give rise to significant increases in the OD of fluids treated thereby, and in this connection the capability of the method of the present invention to achieve effective viral inactivation in fluids with relatively high OD, is a particular advantage. Accordingly in a preferred aspect of the present invention a UV irradiation treatment of the invention is used in combination with a solvent detergent treatment.

In connection with the above it may be noted that different types of virus can have different susceptibilities to various treatments, and it is often necessary to use a combination of different treatments to ensure inactivation of all the different viruses present. A particular benefit of the irradiation treatment of the present invention is that certain types of virus such as CP (canine parvovirus) which are resistant to other readily available treatments, are more or less highly susceptible to irradiation treatment. Thus in a preferred form of the invention for sterilisation of a biological fluid there is used an apparatus or method for UV inactivation of microorganisms according to the present invention, together with at least one other microorganism inactivating procedure.

In accordance with the present invention, the fluid flow is subjected to a very thorough mixing far beyond that required to achieve homogenisation of fluid in conventional applications of static flow mixing means, in order to ensure that all parts of the fluid are brought into the relatively small irradiation zone adjacent the UV-transparent wall means, for a substantially equal residence time period whereby all parts of the fluid may receive a substantially equal UV radiation dosage sufficient for achieving the required log kill, substantially without, though, degradation of the desired fluid components. The number of flow mixing operations to which the fluid flow is subjected will depend on factors such as the nature and efficiency of the individual mixer elements, and the number of passes of the fluid through the passage e.g. 2 passes through a static flow mixing means with 10 mixer elements will provide 2×10=20 mixing operations. Preferably the apparatus of the invention is formed and arranged so that only a single pass is required, in order to avoid any possible contamination and/or incomplete treatment problems arising from returning partly treated fluid to and mixing with, untreated fluid although it will be appreciated that multiple passes can be achieved in a manner which avoids this risk e.g. by using a different container(s) for holding the fluid prior to a succeeding pass(es). A multiple pass system nevertheless has advantages such as reducing the size and capacity of irradiation apparatus required and providing increased operating flexibility through simply varying the number of passes through the irradiation area.

In more detail, it will be appreciated that the number of mixing operations required will depend on the proportion of the passage volume (more exactly the fluid flow volume therein) occupied by the irradiation zone insofar as a thinner or shallower irradiation zone will represent a smaller proportion and thus require a greater degree of mixing. This in turn will depend on inter alia the optical density (OD) of the fluid being treated at the UV radiation frequency being used, the power and intensity of the UV radiation source used, and on the diameter of the passage, as well as on the passage volume occupied by the static flow mixing means being used. Thus, for example, 4.5% HSA has an $OD_{254}$ of 24.5 which would correspond to an irradiation zone depth of the order of 0.4 mm. With an internal tube diameter of 6 mm and a static flow mixing means occupying 50% of the passage volume, this would correspond to around 50% of the fluid flow volume which would in turn require at least 20 mixing operations to ensure the required residence time in the irradiation zone necessary to achieve a $\log_{10}$ kill. With a larger diameter tube the same irradiation zone depth (for the same fluid OD) would correspond to a relatively smaller proportion of the passage volume and hence be expected to require a larger number of mixing operations and mixer elements, though as discussed elsewhere herein, there would normally be used well above the minimum number of mixer elements so that this particular consideration would normally be taken into account automatically.

It should be noted, that in practice the proportion of the tube volume occupied by the static mixer with static mixers of the kind preferably used in accordance with the present invention, decreases with increased tube ID so that the proportion occupied by the fluid increases. Typical values are indicated below:

| Tube ID (mm) | % Tube Volume occupied by fluid |
| --- | --- |
| 6 | 50 |
| 8.5 | 69 |
| 13 | 71 |
| 18 | 74 |
| 24 | 80 |

Where a single pass is used, the static flow mixing means should have at least 20, preferably at least 30 mixer elements desirably at least 40, most preferably at least 50 mixer elements. Advantageously though significantly higher numbers of mixer elements may be used e.g. at least 100 and possibly up to 300 or more mixer elements, albeit that particularly high numbers of mixer elements are generally less preferred in order to avoid creating excessive back pressure in the flow path, although it will be appreciated that a more robust form of apparatus construction may be employed where it is desired to operate at higher pressures. If desired it is also possible to provide a containment vessel around the vessel though which the fluid being treated is passed. At least in the irradiation area the containment vessel should also have substantially UV transparent wall means e.g. of quartz.

As noted above the level of virus inactivation in a given fluid in a given apparatus is proportional to the residence time in the irradiation area. Residence time is however a function of both flow rate and effective length of the irradiation area (i.e. including any multiples of the actual length corresponding to multiple passes through the irradiation area). Having regard to the minimum flow rate required for effective mixing, it will therefore be appreciated that this will in turn impose a requirement for a minimum effective length of irradiation area in order to provide the required residence time at the flow rate used. (This minimum effective length will of course depend on the various other factors which determine residence time, including vessel diameter, OD of the fluid, being treated, and the susceptibility of the micro-organism to be inactivated which is embodied in the constant K. In practice therefore where it is desired to provide for treatment of fluids with, for example, a range of different ODs, and/or containing micro-organisms with different susceptibilities, then the greatest one of the minimum effective lengths required for each of the various different situations, would normally be selected).

Having regard also to the general requirement in accordance with the present invention to minimize damage to the desirable fluid components, the apparatus and method of the invention will normally be arranged to operate more or less closely to the minimum residence time required to achieve the desired level of virus inactivation, corresponding to a maximum flow rate for a given effective length of irradiation area. In this connection we have found that the log kill obtained is substantially proportional to the number of mixer elements provided within the vessel in the irradiation efficiency is maximised when the vessel is substantially filled with more or less the maximum number of mixer elements that can be accommodated therein. Accordingly in a preferred form of the method and apparatus of the invention, there is used a vessel which is substantially filled with mixer elements—at least within the irradiation area. This has the advantages of both maximising uniformity of irradiation exposure thereby maximising log kill and minimising radiation damage to desirable fluid components, as well as maximising internal cooling thereby minimising thermal damage to desirable fluid components. Typically we have found that effective mixing may be obtained in a practical and economic manner with from 50 to 500, preferably from 80 to 350, mixer elements.

With regard to minimising residence time corresponding to maximising of flow rate, it will be appreciated that, above the minimum effective irradiation area length, it is possible to achieve a given desired residence time with a range of different combinations of flow rate and irradiation area length insofar as an increased flow rate can be counter balanced by an increased irradiation area length, and a reduced flow rate by a reduced irradiation area length. Particularly high flow rates are, though, generally undesirable as these require correspondingly large irradiation area lengths which gives rise to increased manufacturing costs, increased space requirements, increased dead volume within the apparatus, increased radiation source requirement etc. In general the effective irradiation area length (corresponding to actual irradiation area length in single-pass systems), should generally be selected so as to be from 100 to 1000% of the minimum effective irradiation area length, preferably from 150 to 700%, advantageously from 200 to 500%, of the minimum effective irradiation area length.

Typically we have found that for a vessel having an internal diameter of around 6 mm, a suitable effective irradiation area length is generally from 30 to 600 cm, preferably from 40 to 400 cm, advantageously from 50 to 300 cm. Suitable flow rates are generally from 40 to 1200 ml/min, preferably from 60 to 600 ml/min, advantageously from 80 to 400 ml/min. It will of course be appreciated that not all flow rate ranges will be practical e.g. a flow rate at the upper end of the range may be associated with excessive back pressure as discussed hereinbefore, when used with an actual irradiation area length at the upper end of the range. With larger diameters of vessel the effective irradiation area length is progressively increased corresponding to the progressive increase in minimum flow rate requirement as discussed hereinbefore. Similarly with larger vessel diameter there is also a proportionate increase in residence time required for a given log kill level. Thus for example we have found that for a vessel having an internal diameter of the order of 18 mm (after shrink-fitting onto the mixer elements) a suitable effective irradiation area length is generally from 100 to 2000 cm preferably from 120 to 1200 cm, advantageously from 150 to 800 cm. Suitable flow rates are generally from 400 to 6000 ml/min, preferably from 500 to 4000 ml/min, advantageously from 600 to 3000 ml/min. Again it will be appreciated that not all conceivable combinations within the length and flow rate ranges will be practical.

With reference to the relationship between minimum flow rate and vessel diameter we have found that the minimum flow rate in ml/min, is generally proportional to the cube of the vessel radius in mm.

It will of course be understood that the minimum residence time in the irradiation zone for effective inactivation will depend on the sensitivity or susceptibility of the particular micro-organism(s) requiring to be inactivated to the treatment used and details of the relative UV radiation dosages required are readily available in the literature.

Although the absolute dose of UV radiation required for a given $\log_{10}$ kill for a given micro-organism can vary by a factor of 10, the relative sensitivity of different viruses is consistent and provides a reasonably reliable predictor of dose or exposure time for a desired $\log_{10}$ kill with any particular virus as shown in the following table based on the publication by Kallenbach N R, et al (1989) "Inactivation of viruses by ultraviolet light" in "Virus inactivation of plasma products" (ed. Morgenthaler J J). Curr. Stud. Hematol. Transfus. Basel, Karger 56 pp 70–82.

TABLE 1

| UVC radiation dose ($\lambda$ = 254 mn) needed for 1 log kill | |
|---|---|
| Virus | Dose (mJ/cm$^2$) |
| Adenovirus 3 | 1.5 |
| Bacteriophage (*E. coli* virus) (0x174) | 3.0 |
| Coxsackie virus A9 | 12.0 |
| Coxsackie virus B1 | 15.5 |
| Echovirus 1 | 11.0 |
| Echovirus 11 | 12.0 |
| Hepatitis B | 11.0 |
| Infectious hepatitis | 5.8 |
| Influenza | 3.4 |
| Poliomyelitis | 3.1 |
| Poliovirus 1 | 11.0 |
| Poliovirus 2 | 12.0 |
| Poliovirus 3 | 10.0 |
| reovirus 1 | 15.4 |
| Rotavirus SA11 | 7.8 |
| Tobacco mosaic virus | 240.0 |

See also, for example, Marx G. et al., (1996) "Protecting fibrinogen with rutin during UVC irradiation for viral inactivation" Photochemistry and Photobiology 63(4) 541–546; and Connacher J. (1986) "The use of UV light for water disinfection" in The Brewer (May Issue).

As indicated above, the required residence time will also depend on the particular log kill level required for the safe use of the treated fluid, which in turn will depend on the micro-organism concerned, as well as the micro-organism contamination level. In practice one would normally seek to provide residence times which achieve a $\log_{10}$ kill of at least 4 for microorganisms such as HIV, Hepatitis B and C, and parvovirus.

In relation to the maximum residence time in the irradiation zone for substantially avoiding significant degradation of the desired fluid component(s), it will be appreciated that this will depend on the susceptibility of the component to degradation as well as the level of degradation acceptable in any given case. In the case of blood components such as albumin and immunoglobulin, degradation is primarily in the form of aggregation of the albumin molecules which is very undesirable because of neoantigen formation whilst in the case of other components such as blood coagulation factors such as Factor VIII, Factor IX, and fibrinogen, degradation is primarily in the form of loss of biological function. Other forms of damage that may be mentioned in this connection include the formation of protein ketone oxidation products. It will be appreciated though that normally residence time will be selected so as to be more or less close to the minimum required for a desired $\log_{10}$ kill in order to minimize possible damage to desired components.

It will also be understood that degradation may occur not only from the effects of the UV radiation as such, but also from any overheating which might arise due to the proximity of the UV radiation source. It is a particular advantage of the present invention, though, that the use of a reasonably fast fluid flow together with a substantial passage diameter significantly greater than that used with previously known thin passage (typically 1 mm thickness) UV irradiation systems which provide a relatively substantial body of fluid through which any absorbed thermal energy is rapidly dispersed by the very thorough mixing, has the effect that overall or localised heating up of the fluid is substantially avoided without the need for any additional fluid cooling measures. Preferably though, at least some cooling, conveniently assisted air flow cooling, is provided to the UV radiation source to help limit the temperature of the lamp tube wall and thus limit thermal transfer therefrom to the vessel.

Preferably, there is used a passage diameter of at least 4 mm, advantageously at least 6 mm, desirably at least 10 mm, for example, from 15 to 40 mm, preferably from 20 to 30 mm. A further significant benefit of using such larger passage diameters, is that it facilitates the use of more efficient UV radiation source arrangements. Typically such sources are in the form of elongate low pressure discharge tubes having a diameter of 25 or 35 mm, though in principle higher intensity sources such as medium and high pressure discharge tubes may also be used. The latter though tend to have the disadvantage of relatively high running temperatures requiring substantial cooling of the discharge tube. The radiation source tubes are preferably used in an annular array for maximizing efficient delivery of UV radiation into an annular irradiation zone inside the passage. With very small passage diameters it becomes impossible to dispose the light source tubes into a suitable geometrical arrangement. It will incidentally be appreciated that the actual UV radiation flux received in the irradiation zone inside the passage will have a more or less complex relation with the flux emitted from the radiation source tubes, due to inter alia the optical effects of the passage walls and the somewhat complex geometrical relationship between the radiation source tubes and the annular irradiation zone. Insofar, though, as the "Flux" component of the formula defining the relationship between $\text{Log}_{10}$ Kill and residence time, will remain substantially constant for a given apparatus configuration, and the main variables such as flow rate, Tube Diameter and OD can be readily measured, the exact value of the Flux component does not need to be known. Any temporal variations in flux may moreover be conveniently monitored by means of chemical actinometry as further discussed hereinbelow.

The vessel may be formed from one or more biologically compatible/acceptable materials such as plastics, biologically inactive metals or alloys of metals, or glasses. Preferably the vessel is formed from plastics such as PTFE, PMMA, PMA, PE, FEP, PVDF, fluorinated polymers or PVC.

In general said UV-transparent vessel wall means is transparent to electromagnetic radiation in the wavelength region of 200 to 400 nm. More preferably, the vessel is transparent in the wavelength region of 220 to 280 nm, however UV-transparency at a wavelength of 254 nm is most preferred. The UV-transparent walls of the device may be made from an inorganic material such as a glass containing silicon oxide. Preferably glasses such as those sold under the trade names of Spectrosil and Vitreosil are used. Alternatively, the wall means may be formed from plastics such as organic polymers, co-polymers and the like such as but not limited to cellulose products (sold under the trade name Cellophane) PTFE, FEP, PVC and PE. In general these have UV transmission properties in the range from 15 to 80% for a typical wall thickness which is generally of the order of 1 mm to 0.5 mm, although we have found in practice that even thinner walls thicknesses (with greater UV transmission) can be used e.g. at least 0.1 mm, preferably at least 0.25 mm. Desirably the wall material, and the thickness thereof used in the vessel wall, is selected to have a UV transmission of at least 60%, preferably at least 70%. In the case of FEP a 150 $\mu$m wall thickness having a $\text{UV}_{280}$ transmission of around 75% has been found convenient.

Preferably the static flow mixing means is of the interfacial surface generator type whereby the fluid passes through said one mixer element which divides the fluid at the inlet of the device into a plurality of substreams, then re-orientates and recombines the substreams, the process being repeated with further elements until a desired degree of mixing has been achieved. Advantageously there is used a static flow mixing means in the form of an elongate helical or spiral screw member having alternate mixer elements of opposite hand (left-right-left etc). Static flow mixers of this kind have been known and used for many years for various purposes such as food and chemical product manufacture, and are commercially available from inter alia TAH Industries Inc of Robbinsville, N.J., USA, Chemineer Inc of North Andover, Mass., USA under the Trade Name KENICS KM, and from Liquid Control Ltd of Wellingborough, England under the Trade name POSIMIXER, and provide very intensive mixing as a result of a combination of a number different mixing effects comprising flow division through repeated division of previously divided streams thus creating a geometric progression of flow division according to the formula $D=2^n$ where D is the number of flow divisions and n is the number of mixer elements; flow reversal whereby the direction of rotation about the longitudinal axis of the mixer is reversed at each mixer element (clockwise—anti-clockwise—clockwise etc.); radial mixing resulting from flow reversal and flow inversion which occurs when fluid close to the centre of each of the separate flows at a mixer element of the device is driven radially outwardly when it encounters the edge of a new mixer element; and resulting inhibition of axial differentiation (corresponding to establishment of axial flow profiles).

In this connection it will be appreciated that it is desirable, particularly with a single-pass apparatus, that the static mixer should be of a form which provides a fluid flow in which there is no significant differential in flow rate across the diameter of the passage so that there is no significant variation in residence time for different parts of the fluid in the irradiation zone. This type of fluid flow in which there is effectively substantially complete radial mixing with no significant longitudinal or axial mixing is known as "plug flow" and the above described helical or spiral type static mixers are particularly effective in providing such fluid flow.

The static mixer elements may be made of various materials which are substantially inert and resistant to damage. In general the material should be non-toxic and resistant to degradation by UV radiation, by the fluids being treated and by any fluid/processing required to be used for cleaning purposes. Suitable materials include inert metals such as stainless steel and resistant plastics materials. PVDF (polyvinlidene fluoride) is a particularly suitable plastics material which is highly resistant to UV radiation.

It will also be appreciated that particular forms of the above described static mixer elements may provide additional benefits such as higher flow rates and/or more efficient mixing, and in this connection there may be mentioned the patented apple-core cross-section spiral mixer elements of the TAH Industries static mixers.

It will be appreciated that, especially with higher flow rates, more or less significant axial forces will be exerted on the static mixer elements by the fluid flow. Accordingly it is generally desirable that these be secured against axial displacement. In the case of glass tube passages this may conveniently be achieved by providing radially inwardly extending projections serving as axial stops. With plastics tubing passages, the tubing may conveniently be shrink formed around the mixer element by thermal treatment so as to reduce the inner diameter of the tubing thereby to tightly grip radially outer portions of the mixer elements, and project, to a greater or lesser extent, radially inwardly thereof between axially spaced apart outer portions of the mixer elements.

The fluid flow supply means may be a pump located upstream of the inlet of the device. Alternatively, the fluid may be supplied to the device by gravity feed. Preferably the fluid flow supply means is provided with adjustable flow rate control means for adjusting the fluid flow rate to a value providing any desired residence time within the limits defined hereinbefore.

Preferably, the total residence time in the irradiation area is from 1 to 100 seconds for blood-based fluids, desirably from 2 to 16 seconds, advantageously from 8 to 14 seconds.

In a further aspect there is provided by the present invention a method of UV-irradiation of a fluid which method comprises:

a) providing an apparatus of the present invention; and
b) passing the fluid through said apparatus and irradiating the fluid within the apparatus with UV-radiation; and
c) wherein the fluid is passed through the apparatus at a flow rate such that the residence time of the fluid in the irradiation zone is not greater than 16 seconds, preferably not more than 8 seconds.

It will be appreciated that it is especially important in a through-flow treatment process to be able to monitor at least to some extent, the consistency of the radiation dose received by the fluid passing through the apparatus, in order to obtain some assurance that the fluid has in fact been safely processed, for example, to ensure that the UV radiation source has not partly decreased its output and hence the FLUX received in the irradiation zone which fact may not necessarily be apparent from visual inspection.

We have now found that UV radiation from UVC and other commercially available UV irradiation lamps can be used to induce a chemical reaction more or less quantitatively and thus the total radiation received over a period of time can be measured. Thus in accordance with yet another aspect of the present invention, there is provided a method of monitoring UV radiation received by fluid flowing through an irradiation area of a UV radiation apparatus comprising the steps of providing an actinometric solution, which solution undergoes a substantially quantitative chemical reaction manifested by a change in absorbance at a predetermined wavelength, upon irradiation with a given dose of UW radiation; passing samples of said actinometric solution through said apparatus, before and after use of the apparatus for UV irradiation of a fluid for viral irradiation therein; and comparing the absorbance changes in said actinometric solution samples. Various actinometric solutions may be used in accordance with the present invention. Alkali metal, alkaline earth metal and ammonium salts of iodide are particularly convenient, the iodide being converted to iodine whose yellow colour may be measured spectrophotometrically at 352 mm. The sensitivity of the iodide solution to the UV radiation dosage may moreover be controlled by adjusting the pH, conveniently using a suitable acid or alkaline buffer such as, for example, citrate or borate, with lower pH providing higher sensitivity. Another suitable actinometric solution which may be mentioned comprises aqueous uridine monophosphate (UMP) which is converted to UMP—hydrate upon irradiation with UV (Marx et al 1996 Photochemistry and Photobiology 63 541–546).

Whilst the most effective and efficient viral kills are generally obtained with relatively short wavelength UV radiation such as UVC which has a wavelength of around 254 nm, various sources may be used providing various different wavelengths, some of which may be outside the UV spectrum and within the visible spectrum. One limitation with conventional UVC sources is that they are of relatively low energy. It may therefore be desirable to use other, higher energy, sources of radiation such as medium and high pressure mercury vapour lamps, and Xenon strobe lamps (which in practice are of such high energy that they normally cannot be rum continuously and must be rapidly pulsed on or strobed in order to avoid damage to the source etc), which provide radiation with longer wavelength UV e.g. UVA and UVB and/or radiation including white light and/or other visible spectrum light.

The invention will now be further described with particular reference to the following examples and accompanying drawings wherein.

Figure 1:
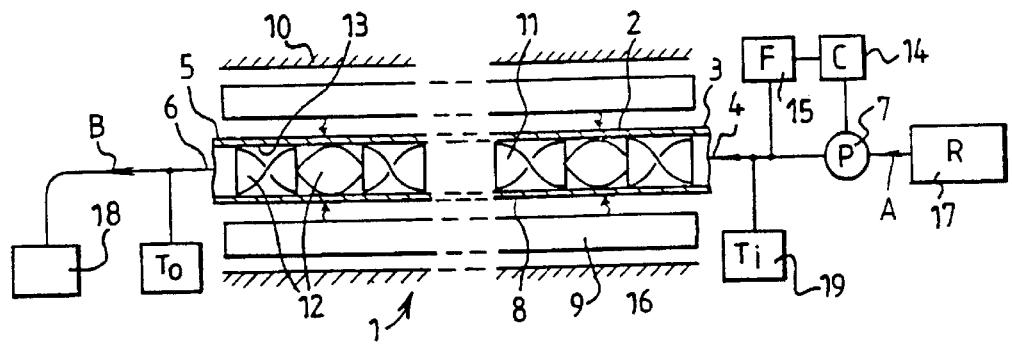
FIG. 1 is a schematic flow diagram of a first apparatus of the present invention.

FIG. 1 shows an apparatus 1 of the present invention comprising a tubular vessel 2 having a first end 3 with an inlet 4 and a second end 5 having an outlet 6. Arrow A shows the direction of flow of the liquid into the device and arrow B indicates the direction of the flow of the liquid exiting the device in use.

A fluid flow supply means 7 is provided to pass fluid through the tubular vessel 2 in use of the apparatus. The fluid supply means 7 is typically a pump which can pump the fluid through the device at a desired flow-rate, for example, a peristaltic pump or a gear pump.

In an alternative arrangement (see FIG. 3) of the present invention the fluid can be supplied to the device 1 by arranging a reservoir 7 of the fluid to be held at a level substantially above the level of the inlet 3 and outlet 5 of the device 1. This arrangement allows the fluid to flow under the influence of gravity from the reservoir 7 through the tubular vessel 2 to the outlet 5 positioned below the level of the reservoir 7.

The tubular vessel 2 of the apparatus 1 is in the form of a silica tube wall means 8. The tubular vessel is substantially cylindrical and has a length of about 50 cm, an internal diameter 6 mm and a wall thickness of about 1 mm.

Four angularly distributed UV-C lamps 9 mounted inside a reflective housing 10 are positioned more or less closely adjacent around the vessel wall means 8 with a typical separation of about 5 mm therefrom. Suitable lamps in this case were those commercially available from Phillips Lighting of Croydon, England with a power rating of 15 W, length of approximately 48.5 cm, and diameter of about 28 mm and sold under the designation TUV-15W. In relation to the control of the exposure of the fluid to the UV radiation, this is conveniently monitored in terms of the residence time of fluid 16 within any part of the UV-transparent wall tubular vessel 2 between the opposed UVC lamps 9, referred to herein as the irradiation area though it will be appreciated that the actual period of time during which any part of the fluid is actually irradiated—corresponding to residence time within the irradiation zone adjacent the walls of the vessel will be rather less than the residence time in the irradiation area, the difference depending on factors such as the OD of the fluid and the diameter of the vessel as discussed hereinbefore.

A static flow mixer 11 extends along the length of the vessel 2 and has a series of 80 mixer elements 12 arranged longitudinally thereon with 40 pairs of alternatively handed screw elements angularly offset from each other by 90°. The mixer device used was of Polyamide and had an outside diameter of 6 mm which was a push-fit inside the silica tube vessel 2. The mixer device used was one commercially available from Metermix Systems Ltd of Wellingborough, England under the designation. The elements 12 in such devices are formed and arranged such that in use the fluid is very thoroughly mixed so that different portions of the main body of the fluid are successively brought within a more or less shallow irradiation zone 12 adjacent the wall 8 of the vessel 2 to be UV-irradiated. In this way substantially all of the fluid is exposed to a similar micro-organism inactivating level of UV-irradiation.

In order to control the fluid flow rate through the vessel, the pump 7 is provided with a control means 14 for adjusting the pumping rate. A flow meter 15 of the Coriolis mass flow type, is provided to monitor the volume of fluid passing through the apparatus and may be used to provide a direct input to the pump controller 14 or could simply provide a read out which can be used by the operator, manually to adjust the controller 14. The fluid 15 to be treated is placed initially in a reservoir 17 and after treatment is collected in a sterile container 18.

The amount of fluid in contact with or close proximity to the vessel wall 8 is relatively small compared to the total volume of fluid present in the tubular vessel 2 at any given time, as a result of which the fluid is substantially self-cooled during UV-irradiation whereby the fluid in the shallow irradiation zone adjacent the tube wall exchanges much of the heat gained during the irradiation with the liquid inside the tube radially inwards of the irradiation zone 13 when the fluid is remixed as it passes from one mixer element 12 to the next. This cooling effect minimises heat damage to the components of the fluid during irradiation. If desired, any temperature rise can be monitored through temperature probes 19, 20 at the inlet and outlet 4, 5 of the vessel 2. In practice the temperature rise is generally limited to about 1 to 2° C.

Although as noted hereinabove, the absolute values of the Flux or Fluence of the radiation are not critical to the successful operation of the present invention, we have estimated this for the apparatus of FIG. 1 in the following manner. The apparatus has a cluster of 4×28 mm o.d. lamps co-linear with a 6 mm i.d. bore (8 mm o.d.) silica pipe at a distance of 7 mm from the pipe surface. The measured flux output of the lamp using a calibrated electronic photometer was 11.8 mW/cm$^2$ 7 mm from the surface of the tube, however, as the pipe and the tube are both curved, the surfaces are not parallel and consequently the flux is not uniform around the circumference of the tube and an averaged intensity about 85% of the peak value was estimated from the manufacturers polar diagrams. Secondly the flux inside the tube is reduced by light absorption, scattering and reflection in the tube wall and surfaces. The manufacturers data for the grade of silica used indicate that about 85% of the flux at 254 nm will be transmitted, thus the light flux at the inner surface of the tube can be estimated as 11.8×0.85× 0.85 mW/cm$^2$ or 8.5 mW/cm$^2$. Similarly for the apparatus of FIG. 3 which used a cluster of 5×40 mm o.d. tubes (TUV-115W RVHO) around a plastic pipe of 18 mm i.d., with a measured flux of 25 mW/cm$^2$ at a distance of 5 mm from the surface of the tube, after allowing for the non uniformity of illumination at the pipe surface (90%) and the transmission of the pFEP pipe (75% at 254 nm according to manufacturers data), the estimated flux at the inner surface of the pipe or tube is 25.0×0.9×0.75=16.9 mW/cm$^2$.

Figure 2:
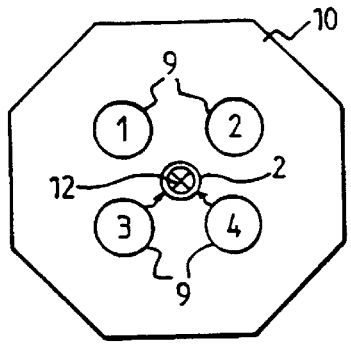
FIG. 2 is a transverse section through the irradiation part of the apparatus of FIG. 1.
Figure 3:
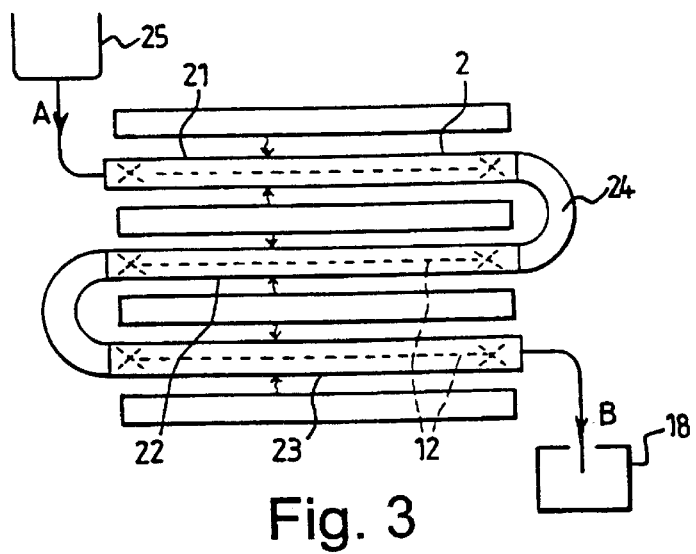
FIG. 3 is a schematic flow diagram of another apparatus of the present invention.
Figure 4:
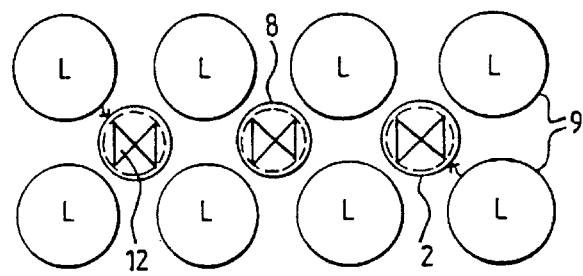
FIG. 4 is a transverse section corresponding to FIG. 2 of the apparatus of FIG. 3.

FIGS. 3 and 4 show another apparatus of the invention in which the parts corresponding to those in the embodiment of FIGS. 1 and 2. In this case the tubular vessel 2 is in the form of three 1.28 m long tubes 21–23 each having an internal diameter of 20 mm (reducing to about 18 mm after thermal shrink fitting onto the mixer elements 12) and a wall thickness of 0.15 mm and made of FEP (fluorinated ethylene propylene), interconnected in series by U-tube connectors 24. The fluid supply means in this case is simply in the form of an elevated reservoir 25 formed and arranged to supply the fluid to be treated under gravity. The UVC source in this apparatus comprises an array of 8 UVC lamps 26 each having a power rating of 115 W also available from Phillips Lighting under the designation TUV-115X RVHO and having a diameter of 40 mm and length of 1.2 m. The lamps 26 are arranged so that four angularly distributed lamps are positioned around each of the vessel tubes 21–23. The treated fluid is again collected in a sterile container 18.

Typically the above described apparatus can be used to UV-irradiate efficiently between 60 and 250 liters of fluid having an $OD_{254}$ of the order of 25, per hour using a vessel with an internal diameter of 18 mm with a Ø×174 $\log_{10}$ kill of at least 4.

Figure 5:
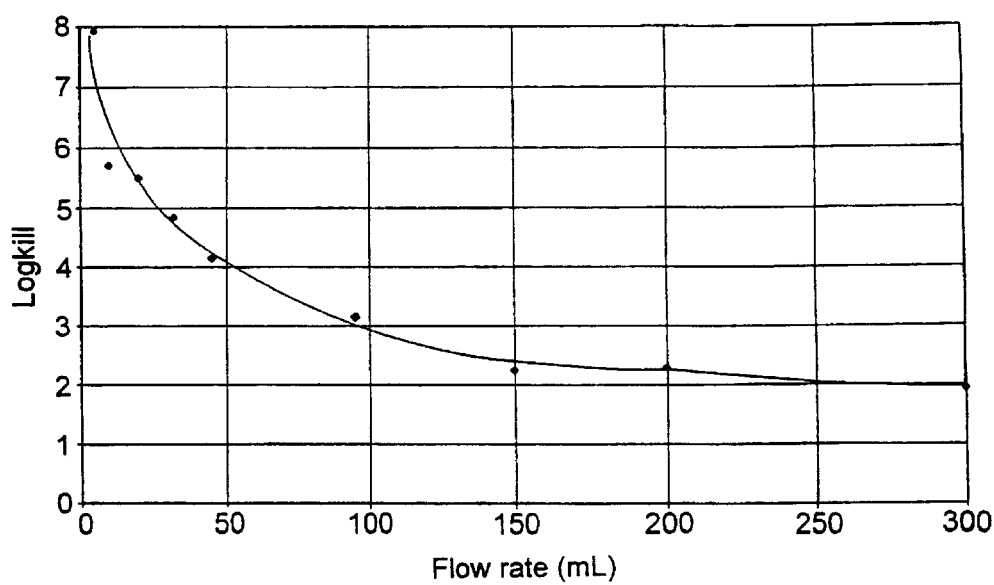
FIG. 5 is a graph of LRV against flow rate for bacteriophage inactivation.
Figure 6:
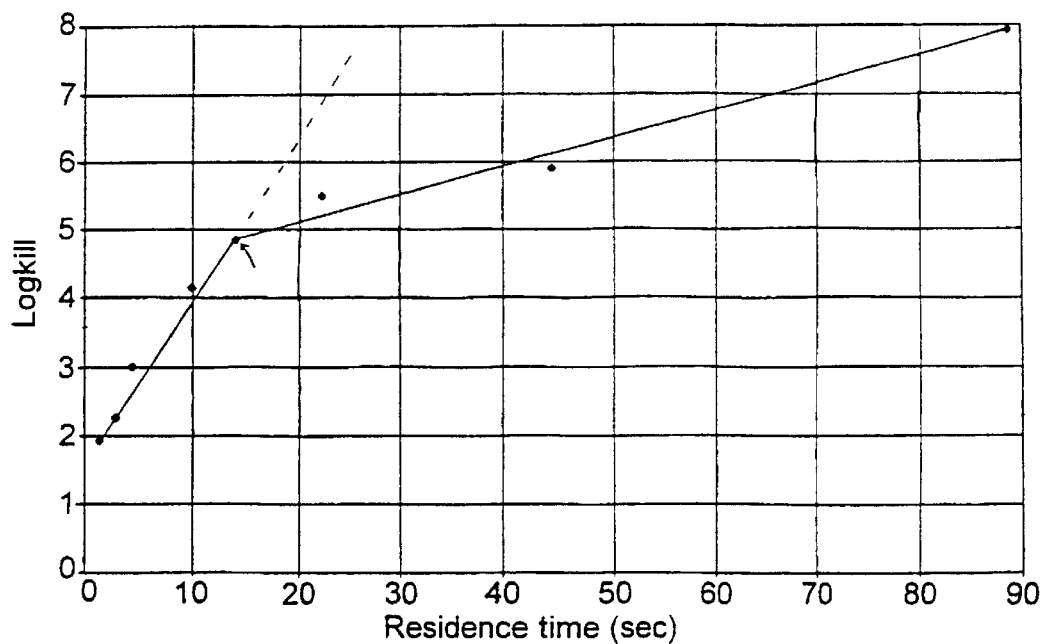
FIG. 6 is a graph of LRV against residence time for bacteriophage inactivation.

The effect of flow rate on mixer efficiency is demonstrated in FIGS. 5 and 6 which show the variation of $\text{Log}_{10}$ kill or Log$_{10}$ Reduction Value (LRV) for the øx174 bacteriophage with flow rate when treated in a 6 mm i.d. tube in an arrangement corresponding to that of FIG. 1. FIG. 5 simply shows the variation of LRV with (volumetric) flow rate. The same experimental results are shown in FIG. 6 but in this case the flow rate has been plotted in terms of the corresponding residence time for the fluid as it passes from the upstream end to the downstream end of the irradiated length of the tube 2. In the latter Figure it may be seen that whilst there is a steady and substantial increase in LRV with reducing residence time (corresponding to lower flow rate) in the residence time range from 2 to 14 seconds, above 14 seconds (corresponding to a flow rate of 32 ml/min), the rate of increase of LRV is dramatically reduced indicating a breakdown in the highly efficient mixing conditions obtaining for flow rates above 32 ml/min. The practical effect of this is that the rate of increase of damage to desirable components of the fluid becomes proportionately much greater which is particularly undesirable. (Similar experiments were carried out for larger diameter tubes and indicated minimum flow rates for efficient mixing of around 230 ml/min for 13 mm i.d.; and around 1000 ml/min for 18 mm i.d.). In general, minimum flow rates for ideal mixing can be calculated from the equation:

$$\text{flow (ml/min)}=1.185\times(r)^3$$

where r is radius in mm. Using this equation, the following minimum flow rates may be derived:

| Tube Diameter (mm) | Tube Radius (mm) | Minimum flow rate (ml/min) |
| --- | --- | --- |
| 6 | 3 | 32 |
| 12 | 6 | 256 |
| 18 | 9 | 865 |
| 24 | 12 | 2050 |

Figure 7:
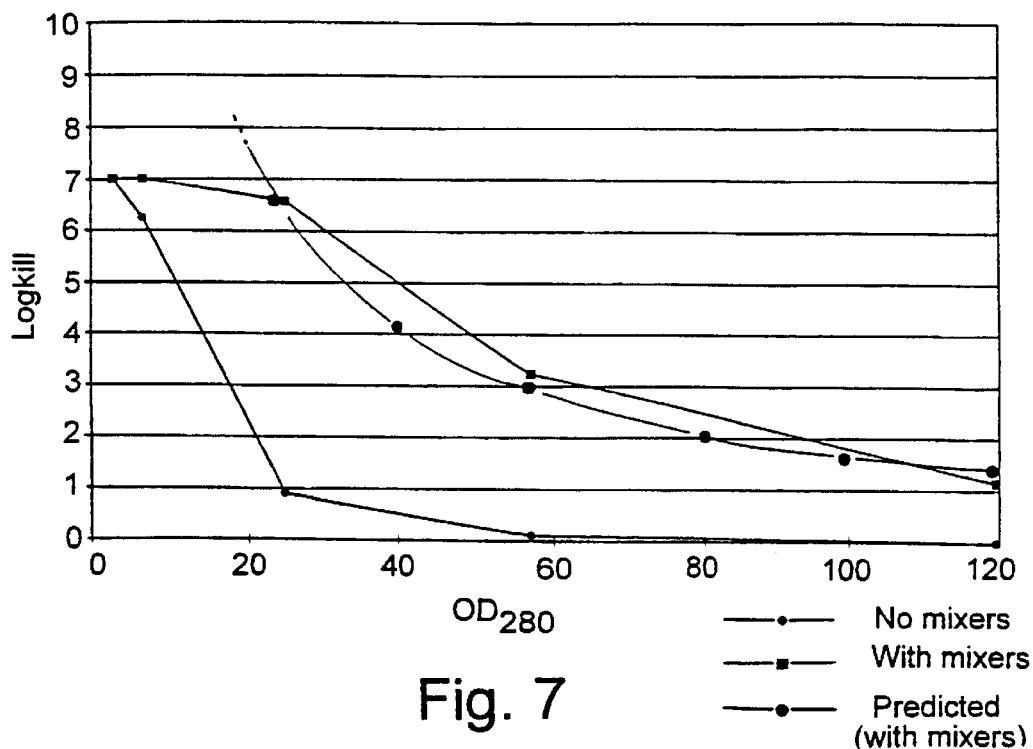
FIG. 7 is a graph of LRV against fluid OD showing the effects of mixing.

FIG. 7 shows the effects of fluid feedstock OD on LRV using an apparatus generally as illustrated in FIG. 1 with a flow rate of 30 ml/min in a 6 mm i.d. tube. Firstly it may be seen that when no mixer elements at all are provided inside the tube, LRV falls very dramatically with OD values which are still in single figures, with little if any useful LRV above an OD of the order of 5 to 10. In contrast when the tube is filled with mixer elements (80 individual elements), an LRV of 4 or more is maintained up to OD values of around 50. (Similar LRV values could moreover still be obtained with even higher OD fluids by increasing residence time i.e. by increasing the length of the tube or decreasing flow rate so long as this does not fall below the minimum flow rate of around 30 ml/min applicable for this diameter of vessel). Finally there is shown the expected variation in LRV with fluid OD as predicted in accordance with the simplified relationship according to the present invention. As may be clearly seen from the Figure, there is very good agreement between the predicted variation and the actual experimentally determined variation over a wide range of fluid OD values. (It will be appreciated that LRV values much above 7 are not very meaningful in practice as micro-organism titres can generally not be measured when they exceed the input titre of the micro-organism.

Figure 8:
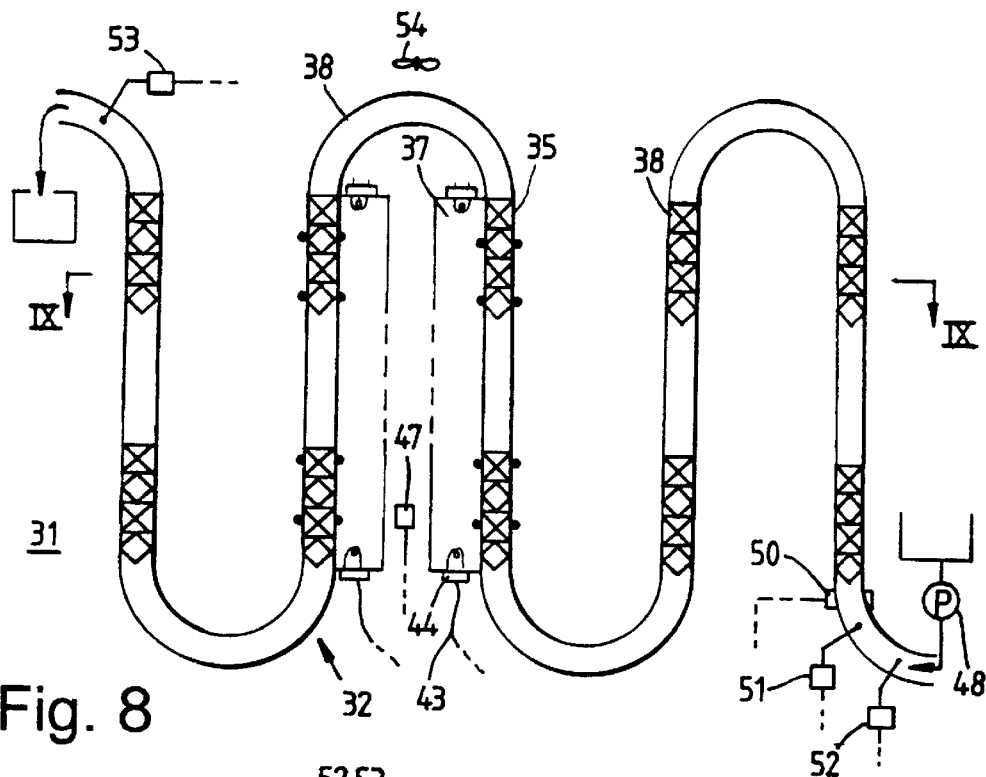
FIG. 8 is a schematic vertical sectional elevation of a production scale apparatus of the invention.
Figure 9:
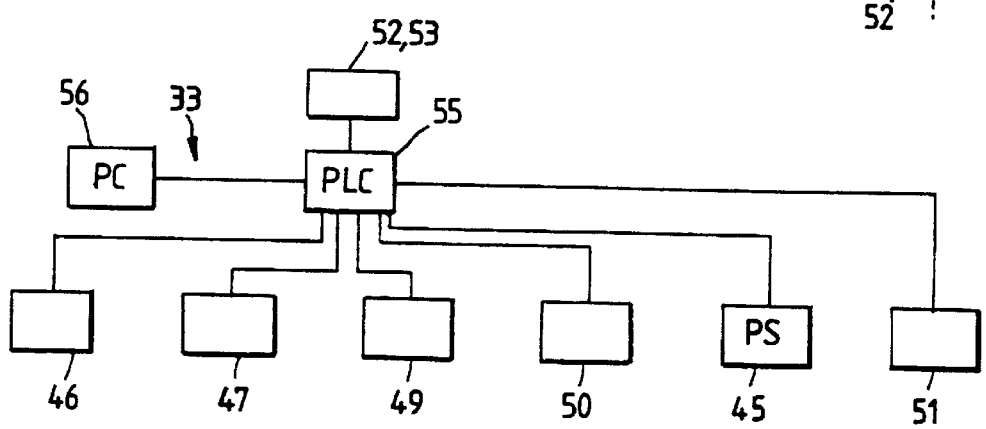
FIG. 9 is a detail transverse section of part of the apparatus of FIG. 8 in the plane IX—IX.
Figure 9:
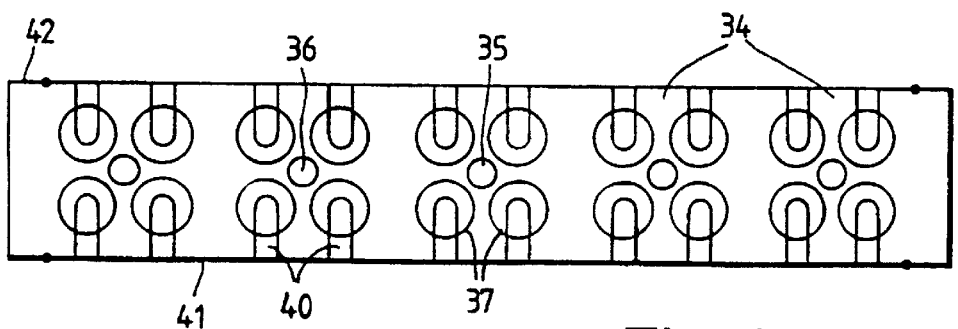

The apparatus 31 of FIGS. 8–9 comprises an optical section 32 and an electrical section 33. The optical section has five vertically mounted cassettes 34 (see FIG. 9), each cassette consisting of one substantially UV transparent flow pipe 35 for process fluid 36 surrounded by a concentrically aligned annular array of four low pressure mercury discharge lamps 37. The individual cassettes are interconnected alternately top and bottom to give a serpentine flow path. The lamps used are Phillips TUV-115W RVHO, 35 mm dia by 1,200 mm length, giving a UV-C power output of approximately 100 mW/cm$^2$ at the surface of the lamp, approximately 85% of the power output is contained in the 254 nm emission line.

The process flow pipes 35 were fabricated from heat-shrinkable DuPont fluorethane polymer (Holscot FEP wall thickness 0.25 mm internal diameter (i.d.) 22 mm before shrinking). Lengths of 1.2 meters of this tubing were loosely assembled with seventy two paired helical mixer elements 38 (MeterMix Pt No 123-608 in PVDF) of 20 mm diameter, assembled sequentially in alternate left and right handed flow, and after heating to approximately 110° C. with a heat gun, the plastic tubing shrank to a final i.d. of 20.5 mm. Individual process flow pipes 35 were interconnected with semicircular bends of stainless steel pipe 38 of i.d. 20 mm (Memtech stainless steel Flanges) using (Metron Technology-Fluoroware Ultrapur Fittings G12-12-FN-1) sanitary connection clamps. Around the circumference of each process pipe section, six 3 mm by 20 mm nitrile Viton (TM) synthetic rubber 'O' rings 39 were spaced at equal intervals along the pipe lengths to act as spacers and ensure alignment between each process pipe 35 length and the surrounding four lamps 37.

The lamps are mounted 40 on hinged door assemblies 41 of an outer stainless steel cabinet 42 providing isolation and optically-tight enclosure to allow easy access for cleaning and maintenance. Electrical connections 43 from the lamps 37 are taken via waterproof end caps 44 out of the optical section 32 and into the electrical section 33. In addition to power supplies 45 to the lamps 37, the electrical section also includes lamp monitoring means 46 for monitoring individual lamp performance by continuous measurement of lamp voltage drop and current. Lamp output is also independently and individually monitored by silicon photodiode sensors 47 fitted with 254 nm interference filters.

The flow rate of the process fluid is controlled via a gear pump 48 with a flow rate controller 49 (SSP Rotary Lobe Pump Pt No SR/2/018/S5 driven by Eurotherm Drive IPC 102/80B-4AC) over the range from 0.5 to 5.0 L/min and flow is independently measured in a mass flow meter 50 (Hamall-Crone, Coriolis Mass Flow Meter MFM4085 K/F) to ensure that set flow rates are accurately maintained throughout the process run. Under typical conditions for 4.5% albumin, the flow rate is set at 4.2 L/min+/−20% and this will process 1,000 liters of albumin in about 4 hours. The pressure of the feedstock flow immediately on exiting the pump and prior to the flow meter is monitored continuously with a pressure meter 51, as well as the temperature at the inflow and outflow connections using temperature sensors 52, 53. The air temperature within the optical enclosure is also monitored and controlled by means of a sealed recirculating air conditioning unit 54. The process operation is supervised and monitored by a programmable logic controller 55 that can be interfaced directly to a SCADA (Supervisory Control and Data Acquisition) processing plant control system or a personal computer 56. Between fluid processing operations, the internal flow path is cleaned and sterilised by 1N NaOH, and when not in use, the flow path is kept filled with sterile pyrogen free water.

Further preferred features and advantages of the invention will appear from the following examples of use of apparatus of the invention provided for the purposes of illustration.

EXAMPLE 1
Irradiation of Human Serum Albumin (HSA)

A standard HSA 4.5% w/v aqueous solution ($OD_{254}$= 24.5) as used in everyday medicine for restoring blood volume after shock etc., was prepared from pooled plasma and inoculated with becteriophage Øx174 ($10^8$/ml infectious doses). The solution was pumped through a production-scale UV irradiation device (using UVC lamps having a maximum radiation energy at a wavelength of around 254 mm) (generally similar to the apparatus of FIGS. 3 and 4 as described hereinbefore). The fluid was passed through three 18 mm i.d. FEP tubes (each 1.28 m long and containing 80 mixer elements) arranged in series, at a flow rate of 4.2 L/min. Each tube was surrounded by 4 UVC lamps. Tests with a calibrated photometer were used to measure UV radiation intensity at the tube surface and this was found to be 25 $mW/cm^2$. The stability of the Flux irradiance level was confirmed both pre- and post-irradiation by chemical actinometry using aqueous sodium iodide (1% w/v) and monitoring generation of free iodine (through increase in absorption at 352 nm) as further described in Example 5 hereinbelow.
Results This arrangement enabled 1000L HSA 4.5% to be processed within 4 hours and achieve a Bacteriophage log kill of 4.5 determined by a conventional phage assay. Typically, irradiation caused the albumin dimer fraction (as measured by gel filtration 8) to increase from its original level of 5.4% to 6.1%.

Aggregate levels of 8% (components with molecular weight >$2 \times 10^6$ Da as measured by gel filtration) were unchanged after gel filtration treatment. Temperature increase after irradiation of the fluid which had a starting temperature of 20° C. was typically limited to about 1° C.

EXAMPLE 2
Irradiation of Human Plasma

Pooled human plasma ($OD_{254}$=55.0) inoculated with Øx174 (amount $10^8$ pfu/ml) was pumped through a laboratory-scale irradiation device (254 nm) generally similar to that of FIGS. 1 and 2. The fluid was passed through a single 6 mm i.d. silica tube (48.5 cm) long containing 80 mixer elements) surrounded by four UVC lamps providing a UV radiation inter alia at the tube surface of 10 $mW/cm^2$. The flow rate was 40 ml/min (2.4 L/h) providing a residence time of 11.1 sec inside the irradiation area in the tube portion between the UV (lamps). Lamp radiation intensity and irradiance were determined as described in Example 1.
Results Typically, LRV as determined using the procedures described in Example 1 was between 3.6 and 4.0. Temperature rise of fluid with a starting temperature of around 20° C. was 1° C. after irradiation. Recoveries of plasma components (on the basis of their retained biological activity as determined by means of clotting assays were as follows: FVIII:C 80–90%, FV 75–80% and fibrinogen 75–85%.

EXAMPLE 3
Irradiation of Human Immunoglobulin (IgG)

IgG (150 g/L; $OD_{254}$=200) inoculated with Øx174 ($10^8$ pfu/ml) was placed in a cooled reservoir (at 4° C.) and recirculated through an apparatus as described in Example 2 at a flow rate of 100 ml/min until a period equivalent to 24 passes had elapsed (corresponding to a total residence time of 106 sec in the irradiation area inside the tube). Lamp intensity and irradiance were measured as in Example 1.
Results Typically, LRV (determined as before) was 4.2 and aggregate levels (molecular weight >$2 \times 10^6$ Da) (determined as before) increased from 4.7% to 5.2%. In functional assays, irradiated IgG showed a 10 to 15% decrease in anti-streptolysin 0 antigen and a 10% decrease in anti-rubella antibody levels.

EXAMPLE 4
Inactivation of Mammalian Virus

Samples of human albumin (4.5% concentration) were inoculated with a selection of mammalian viruses and processed using similar apparatus and procedure to that described in Example 2 but with a slightly lower flow rate of 30 ml $min^{-1}$ providing a residence time of 14 seconds inside the irradiation area in the tube portion between the UVC lamps. The viruses were chosen in view of, inter alia, their general resistance to heat treatment and/or solvent detergent treatment. Although as noted hereinbefore different individual viruses generally have different susceptibilities to UV irradiation, the samples were all treated under the same conditions: at a flow rate of 30 ml $min^{-1}$.
Results The LRVs obtained for the viruses treated are presented in Table 2.

TABLE 2

| Mammalian Virus LRVs | | |
| --- | --- | --- |
| Virus | Genome/type | LRV |
| Sindbis | Ss RNA | >3.2 |
| SLFV (Semliki Forest Virus) | Ss RNA | >4.3 |
| SV40 (Simian Virus 40) | Ds DNA | 4.2 |
| CPV (Canine Parvovirus) | ss DNA | >6.0 |
| Reovirus-3 | ds RNA | 3.6 |
| HSV (Herpes Simplex Virus) | ds DNA | 2.5 |
| 0X174 | Ss DNA | 6.2 |

It will be seen from both Table 1 (hereinbefore) and Table 2 that the absolute and relative sensitivity of the *E coli* bacteriophage Øx174 can be represented as an internal standard to predict the relative likely kill of any other viruses represented in these tables. Thus for instance, in table 1, it can be predicted that by comparing Adenovirus 3 susceptibilty to Bacteriophage (*E.coli*) (Øx174) susceptibilty, one can predict that for any given set of irradiation conditions, the log kill of Adenovirus will be twice that of bacteriophage and conversely that the log kill of Infectious hepatitis would be approximately half that of Bacteriophage. Similarly, in the table of results for example 4 above, it can be predicted that under any given set of irradiation conditions, the log kill of canine parvovirus will equal or exceed that of bacteriophage Øx174 whereas the log kill for sindbis will be about half of that for bacteriophage phix174. Thus by including a spike of bacteriophage Øx174 in any given product and set of run conditions and measuring its actual log kill, it is possible to predict the likely log kill of any other virus. We have found that it is possible to reproducibly obtain log kills of Øx174 consistently, under fixed conditions of eg 4.2+/-0.2, thus giving a good degree of confidence in the above predictions.

EXAMPLE 5
Chemical Actinometry Using 1% Sodium Iodide

1% (w/v) sodium iodide in 5. mM tris-HCl pH 7.5 pumped through the irradiation device under the same conditions as those used for the treatment of albumin fluid being monitored. In the case of 4.5% human serum albumin, this would entail the sodium iodide solution being pumped through the production-scale device (already described) at a flow rate of 4.2 L/min. A volume equivalent to the dead volume was discarded and a sample of the irradiated sodium iodide which was about 300 mls) solution collected for spectrophotometric measurement at 352 nm (to be carried out not less than 2 hours after irradiation). The device was flushed with saline before passing through the albumin fluid for irradiation treatment. After completing irradiation of the albumin fluid, the actinometry step was repeated in the manner already described. An $OD_{352}$ of 1.0 corresponded to a fluence of 100 mJ/cm$^2$.

The iodide actinometry reagent can moreover be altered in sensitivity to suit the experimental conditions used, if required. Thus we routinely use 1% NaI in 50 mM Tris pH 7.5 but the sensitivity of this reagent can be increased considerably by lowering the pH to eg 3.0 or it can be lowered considerably by raising the pH to 9.2 with buffers such as citrate or borate respectively. The iodide actinometry reagent can be calibrated in absolute units (mJ/cm$^2$) by using the potassium ferrioxalate reagent as described by Jagger,J., (Potassium Ferrioxalate Actinometry, in "Introduction to Research in Ultraviolet Photobiology" 1967, pages 137–139. Prentice-Hall, New Jersey). The comparison is most conveniently carried out in e.g. a small laboratory scale device such as that of FIGS. 1 and 2 using a 48.5 cm length of 6 mm i.d. silica tubing and restricting the illuminated length of pipe to 2.5, 5.0, 7.5 cm etc by wrapping in aluminum foil. This is necessary because the sensitivity of the ferrioxalate reagent is greater than that of the iodide at pH 7.5. A graph can then be constructed relating the optical density of the iodide solution at 352 nm to the corresponding fluence (flux times residence time in seconds) in mJ/cm$^2$. The figure of flux can be obtained for each machine configuration by dividing the observed fluence by the residence time of any particle in the illuminated (irradiated) section (in seconds). FIG. 6 (???) illustrates the calibration curve we obtained for converting iodide A352 nm figures into fluence, which should be independent of the machine but will vary with the pH of the iodide reagent. There are significant advantages in using the iodide actinometric reagent described herein over existing methods. Unlike the uridine monophospate reagent, the reagent iodide produces an increase in optical density with exposure and the spectral change is visible to the naked eye, alerting the operator to correct function of the apparatus. The colour change is immediate and does not have to be sampled off-line for titration as is required for the ferrioxalate method and this allows for continuous or intermittent automated on line actinometry using eg a flow spectrophotometer. An additional advantage of the iodide reagent is that it can be adjusted in sensitivity to suit the exposure dose to be used in the process, which allows for a wide dynamic range, unlike the ferrioxalate reagent which tends to go off-scale in most practical applications. A further advantage of the iodide reagent is that it is cheap and easy to prepare and store in bulk prior to use which is convenient for large volume runs when calibrating or monitoring full scale process apparatus in an industrial environment.

EXAMPLES 6 TO 9
Irradiation of Human Album

The following procedures were used to measure and determine the required parameters for the log kill relationship according to the method and apparatus of the invention.

The viscosity of the Human Albumin solutions (4.5% and 20% v/v) in this study was measured by a commercially available Synchro-Lectric Viscometer (Brookfild Engineering Laboratories, Stoughton, Mass., USA), which rotates a cylinder or disc in a fluid and measures the torque necessary to overcome the viscos resistance to the induced movement. The measurement is accomplished by driving the immersed element, which is called a "sprindle", through a beryllium copper spring—the degree to which the spring is wound indicated by the position of the red pointer on the Viscometer dial, is proportional to the viscosity of the fluid for any given speed and sprindle. The viscosity was found to be 1.36 cp for 4.5% HA and 5.0 cp for 20% HA.

The density of 4.5% and 20% Human Albumin solutions was found to be 1010 and 1051 kg/m$^3$ respectively at 20° C., by measuring the weight of a known volume of protein solution at a given temperature and calculating the density therefrom.

EXAMPLE 6
Determination of Minimum Flow Rate with 4.5% HA

Figure 10:
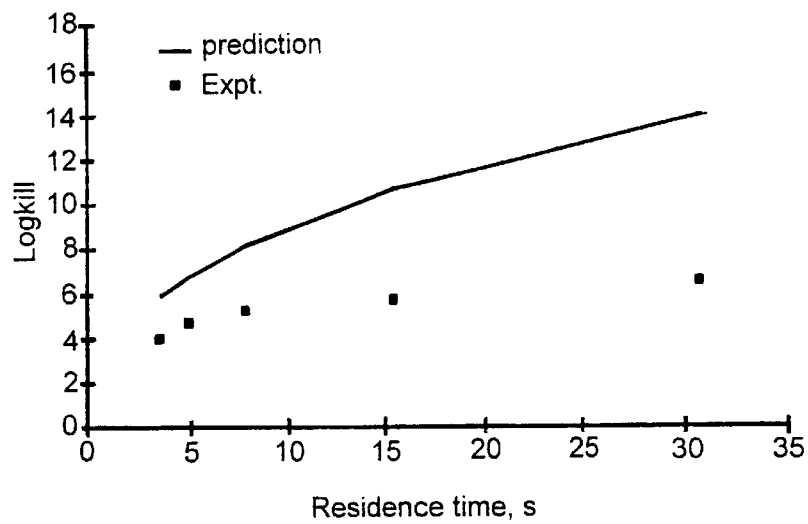
FIG. 10 is a graph of LRV against residence time for 4.5% Human Albumin irradiation indicating a minimum flow rate.

Batches of 4.5% Human albumin were irradiated generally as described in Example 2, at a series of different flow rates. The log kill (LRV) was determined for each run and plotted against the Residence times s determined from the flow rates as shown in FIG. 10. The log kill predicted from the general relationship according to the present invention as determined from the measurements obtained (given below) is also shown, from which it may be seen that above a residence time of the order of 10, the experimental log kill departs substantially from the predicted log kill rate, and little increase in log kill with increased residence time (corresponding to reduced flow rate) is obtained. Taking into account the density, viscosity and linear flow rate corresponding to this residence time, it was found that the departure from prediction occurred at a Reynolds number of the order of 50.

Results—(for UV Irradiation Using 4×15 w UVC Lamps with 6 mm Internal Diameter Silica Glass Tube 36 cm Long)

| (volumetric) Flowrate (ml/min) | Log kill | Reynolds Number |
|---|---|---|
| 5 | 7 | 13.1 |
| 10 | 6 | 26.2 |
| 20 | 5.4 | 52.4 |
| 32 | 4.8 | 83.9 |
| 45 | 4.1 | 118.0 |
| 174 | 2.3 | 456.3 | using the above minimum flow rate determination, it is possible to predict minimum flow rate ($u_{min}$) for other tube diameters and other fluids using the relation: $U_{min}=50\ \mu/d\rho$ wherein $\mu$, d and $\rho$ all have the same meaning as before.

| Solution | Pipe ID, mm | Min Flowrate, ml/min |
|---|---|---|
| 4.5% HA | 10 | 33 |
| 4.5% HA | 13 | 43 |
| 4.5% HA | 20 | 67 |
| 20% HA | 6 | 74 |
| 20% HA | 10 | 123 |
| 20% HA | 13 | 160 |
| 20% HA | 20 | 246 |

EXAMPLE 7
Minimum Flow Rate Determination Using Actionmetry

Figure 11:
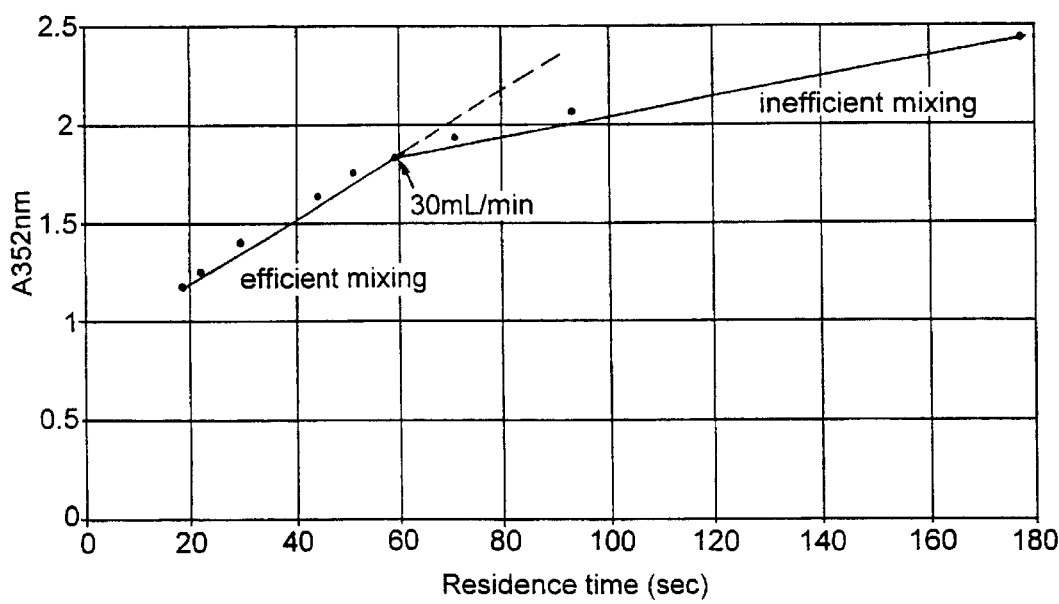
FIG. 11 is a graph of actionmetric measurements using different residence times also indicating a minimum flow rate.

Batches of 1% sodium iodide solution at pH7 were irradiated generally as described herein before, in a 194 cm long 6 mm ID silica tube, using different flow rates. The resulting Absorbance values of the irradiated solutions were plotted in FIG. 11 against flow rate in the form of residence time in seconds. As may be seen from FIG. 11, the Absorbance increases linearly with increased residence time (corresponding to increased exposure time to irradiation), up to a residence time of about 60 seconds corresponding to a flow rate of about 30 ml/min which in turn corresponds to a Reynolds number in this case of about 50. with further increased residence time corresponding to lower flow rate and lower Reynolds number, the rate of increase in Absorbance is substantially reduced thereby also indicating a reduced mixing efficiency.

EXAMPLE 8
Determination of Fluid Property Function in Relationship Between Log Kill and Fluid Irradiation Treatment Parameters UV irradiation of high OD fluids is dependent on the UW penetration depth into the fluid and hence the proportion of the total passage volume receiving the UV radiation in an effective irradiation zone, and on the replacement of the fluid in the irradiation zone by the main body of fluid in the middle of the passage. The latter depends on the mixing means employed. With a static mixer of the kind used herein there is obtained a highly efficient radial mixing (between radially inner and radially outer portions of the passage) and this is a function of the Reynolds Number of the fluid being mixed i.e. f(Re). Taking this into account, the log kill obtained is governed by the following relation:

$$\text{Log } kill = kf(Re) \frac{I(\rho\mu)}{OD \cdot d}(L/Re)$$

wherein $\mu$ is fluid viscosity in c$\rho$, $\rho$ is fluid density in kg/m$^3$, d is fluid passage diameter in mm, Re is Reynolds Number, L is effective passage irradiation length, OD is optical density of the fluid at the intensity at inside wall of passage in mW/cm$^2$.

The above relation may be arranged as:

$$kf(Re) = \frac{\log kill}{L/Re} \cdot \frac{OD \cdot d}{I(\rho/\mu)}$$

which can be expressed as $$kf(Re) = K\, Re^m$$

Figure 12:
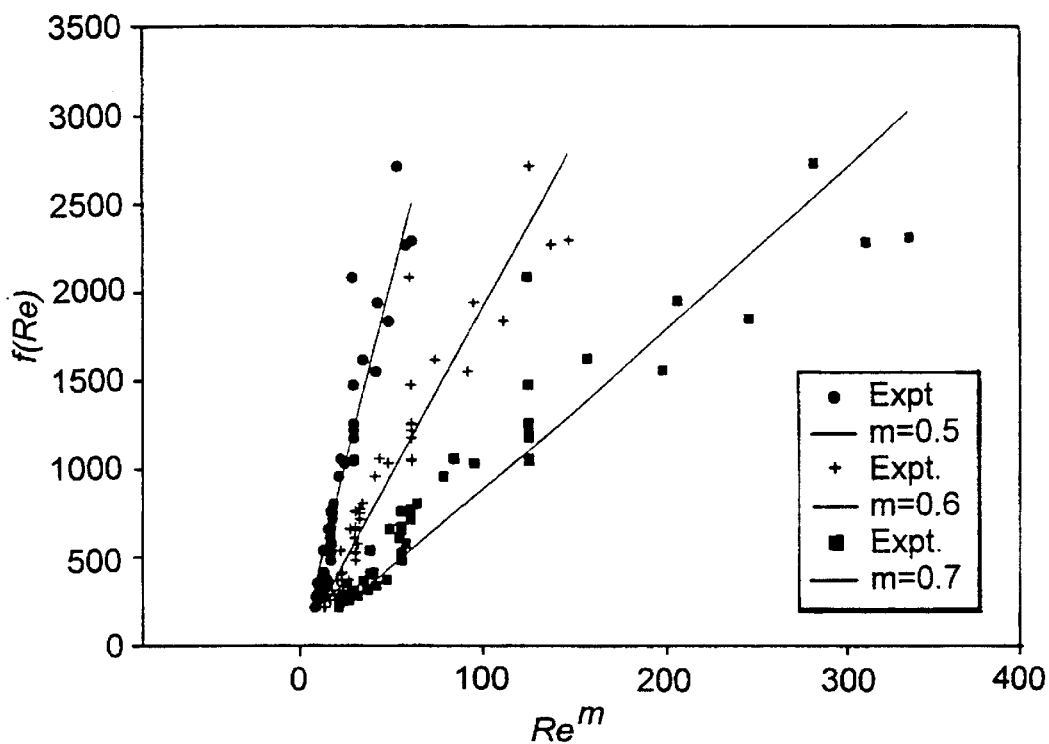
FIGS. 12 and 13 illustrates the regression procedure used to determine the Reynolds Number function index.
Figure 13:
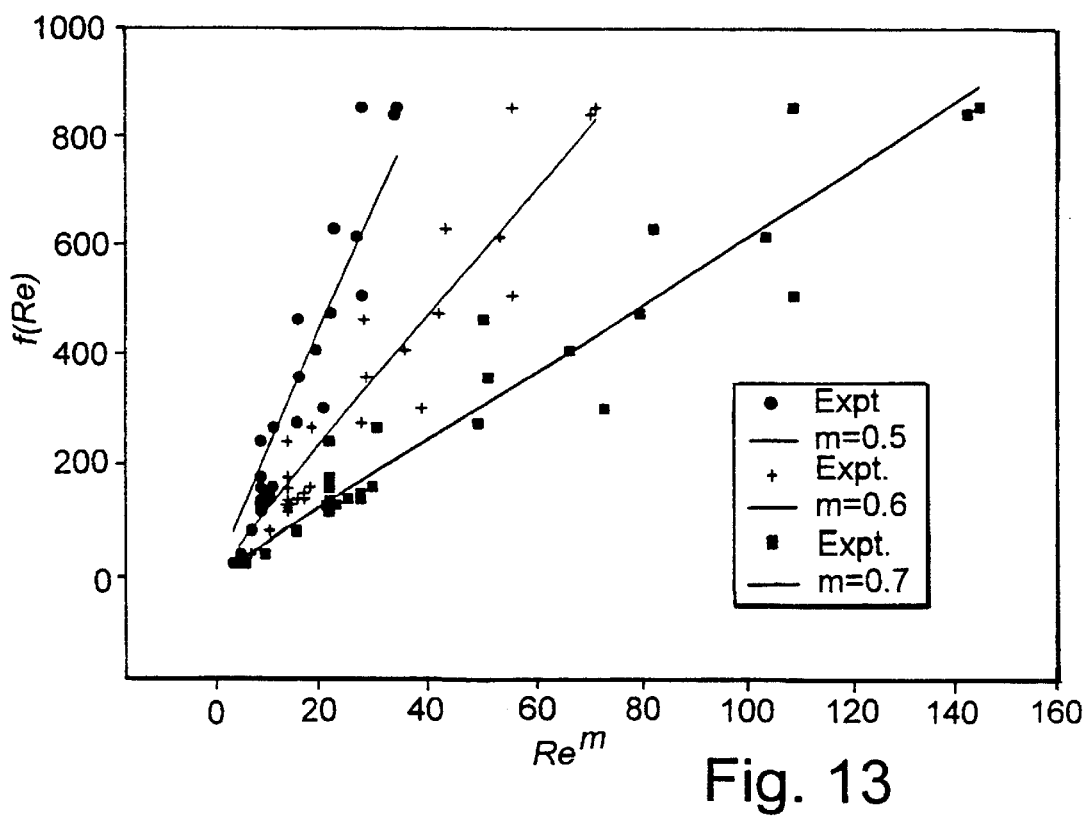

The constant K and index m were obtained from the experimental log kill measurements and values of the other parameters using labscale and larger scale apparatus (FIGS. 1 & 2, and FIGS. 3 & 4, respectively), through regression. As the same form (geometry) of static mixer was used in both apparatus, the index m was kept the same for both during the regressions. As shown in FIGS. 12 and 13, regressions were made at a set of values for m ranging from 0.5 to 0.7 and the best fit was found at m having a value of approximately 0.6. (Note—in view of the less efficient mixing at low rates corresponding to Reynolds numbers below 50, less significance was attached to measurements obtained at such low flow rates). With the above obtained value of 0.6 for the index m, the relationship for predicting log kill then has the following form:

$$\log kill = K \frac{T_m(\rho/\mu)}{OD \cdot d} \frac{L}{Re^{0.4}}$$

in which K is dependent on the susceptibility of the virus type to inactivation by the UV radiation, as well as the power of the UV radiation source, and can be determined from a few test runs. (Tm is relative UV transmissibility of tube wall i.e. $T_m = k'\, I$ where I as the same meaning as before and k' is a constant corresponding to the particular UV radiation source and setup, used.

EXAMPLE 9
Irradiation of Human Albumin

Figure 14:
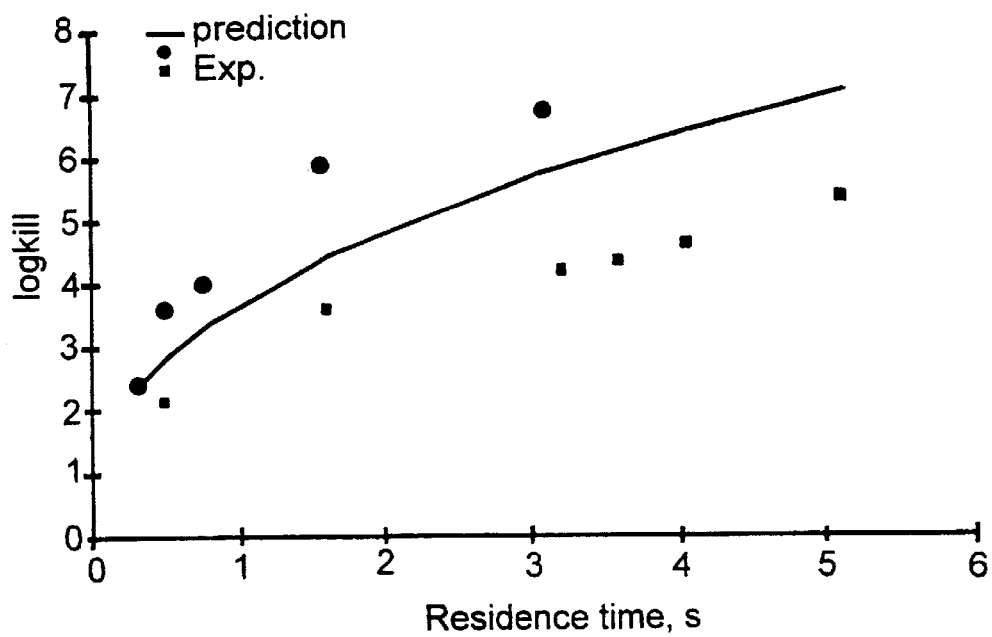
FIGS. 14 and 15 are graphs of log kill against residence time for bacteriophage inactivation in Human Albumin solutions.

A standard HA 4.5% w/v aqueous solution (OD$_{254}$=12.8) inoculated with bacteriophage Ø×174 (10$^8$/ml infections doses) was treated in a laboratory scale apparatus similar to that of FIGS. 1 and 2 as generally described hereinbefore, in two series of experiments each covering a range of different flow rates corresponding to different residence times. Viscosity and density were determined as described hereinbefore. The experimental log kills obtained were plotted against residence time as shown in FIG. 14 and compared with predicted log kill (continuous line) from the general relationship according to the present invention using the above fluid viscosity and density data, Reynolds Number function parameters (m=0.6, K=0.117), and apparatus parameters (d=6 mm, L=36 cms, mixer element volume 50%). As may be seen from FIG. 14 the two series of log kill measurements are closely similar in form and value to the predicted log kill.

Figure 15:
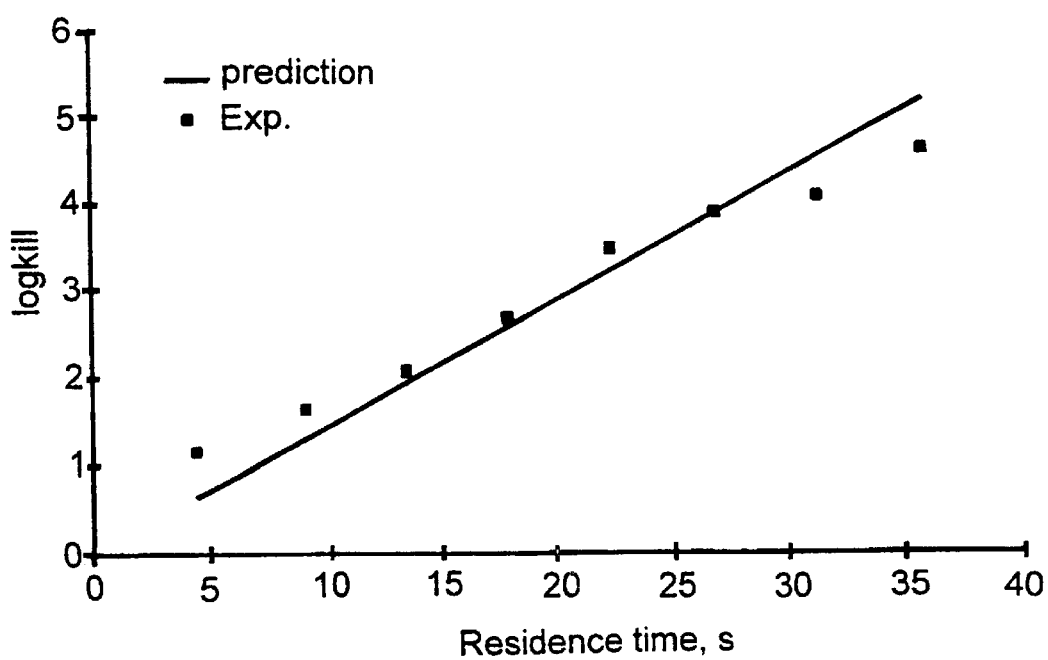

It will be appreciated that increased residence time can be obtained by means of increasing the number of passes of the fluid through the irradiation zone without any change in flow rate, rather than changing the fluid flow rate and velocity u. In this case it will be apparent that there will be no change in the Reynolds number and the relationship between log kill and residence time will become linear as illustrated in FIG. 15 which compares the experimental results obtained using a 20% w/v Human Albumin solution in a large scale apparatus with an 18 mm ID FEP fluid passage tube.

It is intended that the foregoing examples are not limiting to the scope of the present invention and that it will appreciated that various modification may be made to the foregoing without departing from the scope of the present invention.

What is claimed is:

1. A method of UV-irradiation of a biological fluid containing a desired component and a contaminating microorganism, which method comprises the steps of:

a) providing an apparatus comprising a longitudinally extending vessel having wall means of a UV-transparent material disposable, in use of the apparatus, in close proximity to a UV radiation source within an irradiation area and having an inlet and outlet and a passage means formed and arranged so as to define a flow path extending therebetween which is substantially free of substantial discontinuities so as to avoid substantially turbulence in fluid flowing therealong in use of the apparatus, and having an irradiation zone adjacent said UV-transparent wall means for receiving UV radiation from said UV radiation source, in use of the apparatus, said passage means having a static flow mixing means with a multiplicity of mixer elements for repeatedly subjecting the fluid flow to a mixing operation comprising dividing and re-mixing of the fluid flow, in use of the apparatus, which static flow mixing means extends along said flow path along at least said irradiation zone, said vessel having an internal diameter, d, of at least 4 mm, and said apparatus including fluid flow supply formed and arranged for passing fluid through said vessel, in use of the apparatus; and b) passing said fluid through said vessel so that said fluid is subjected to at least 20 said mixing operations, at a fluid flow rate not less than a minimum flow rate corresponding to a maximum fluid residence time within said irradiation area required for efficient mixing as indicated by the maintenance of a substantially close relation between actual log kill and log kill as predicted by the below indicated relationship, with increasing residence time which obtains above said minimum flow rate and at a fluid flow rate not greater than a maximum fluid flow rate corresponding to a minimum residence time in said irradiation area required for effective inactivation of said contaminating micro-organism by providing a desired log kill of said micro-organism, and not greater than that at which significant degradation of said desired component occurs, wherein said minimum residence time in said irradiation area is defined in accordance with the following relationship:

log 10 kill=$K$×Flux×Residence time×$Z$/OD×Tube Diameter wherein Flux indicates the amount of UV radiation incident on the passage containing the fluid flow in the irradiation area immediately inside the passage wall, in mW cm$^{-2}$, wherein OD is the Optical Density of the fluid at the wavelength in the region where substantial virus inactivation takes place;

K is an empirically derived constant;

Tube Diameter is the internal diameter, d, of the vessel in the irradiation area, in cms; and $$Z=u(\rho/\mu)/Re^m$$

wherein u is fluid flow velocity in cm/sec, $\rho$ is fluid density in kg/m3, $\mu$ is fluid viscosity in cp, Re is the Reynolds number of the fluid whose value is defined by the formula Re=du$\rho$/$\mu$ where d, u, $\rho$ and $\mu$ have the same meaning as before, and m is a characteristic of the static mixer system whose value is determined experimentally, whereby substantially the whole of the fluid may be exposed to a similar micro-organism inactivating level of UV-irradiation while minimizing damage to the desired component(s) of the fluid.

2. The method according to claim 1, wherein a minimum residence time not less than that required for a 4 log kill of said contaminating micro-organism is employed.

3. The method according to claim 1, wherein said minimum residence time not less than 1 second is employed.

4. The method according to claim 1, wherein said maximum residence time not greater than that at which 10% aggregation and/or 20% loss of biological activity of said desired component occurs is employed.

5. The method according to claim 1, wherein UV radiation having a wavelength of from 250 to 280 nm is employed.

6. The method according to claim 3, wherein the fluid is passed through the apparatus at a flow rate such that the residence time of the fluid in the irradiation zone is from 1 to 100 seconds.

7. The method according to claim 6, wherein said residence time is from 2 to 16 seconds.

8. The method according to claim 1, wherein the method further comprises introducing a protective agent into said fluid.

9. The method according to claim 1, wherein the method further comprises at least one other micro-organism inactivating method.

10. The method according to claim 9, wherein said at least one other micro-organism inactivating method is selected from the group consisting of heat treatment and detergent treatment.

11. A method of setting the fluid flow supply means of an apparatus for use in the UV-irradiation of a biological fluid containing a desired component and a contaminating micro-organism, which apparatus comprises a longitudinally extending vessel having wall means of a UV-transparent material disposable, in use of the apparatus, in close proximity to a UV radiation source within an irradiation area and having an inlet and outlet and a passage means formed and arranged so as to define a flow path extending therebetween which is substantially free of substantial discontinuities so as to avoid substantially turbulence in fluid flowing therealong in use of the apparatus, and having an irradiation zone adjacent said UV-transparent wall means for receiving UV radiation from said UV radiation source, in use of the apparatus, said passage means having a static flow mixing means with at least 20 mixer elements for repeatedly subjecting the fluid flow to a mixing operation comprising dividing and re-mixing of the fluid flow, in use of the apparatus, which static flow mixing means extends along said flow path along at least said irradiation zone, said vessel having an internal diameter d of at least 4 mm, and said apparatus including fluid flow supply means formed and arranged for passing fluid through said vessel, in use of the apparatus; which method comprises the steps of:

determining a minimum flow rate corresponding to a maximum fluid residence time within said irradiation area required for efficient mixing as indicated by the maintenance of a substantially close relation between actual log kill and log kill as predicted by the below indicated relationship, with increasing residence time which obtains above said minimum flow rate and determining a fluid flow rate not greater than a maximum fluid flow rate corresponding to a minimum residence time in said irradiation area required for effective inactivation of a said contaminating micro-organism by providing a desired log kill of said micro-organism, and not greater than that at which significant degradation of said desired component occurs, wherein said minimum residence time in said irradiation area is defined in accordance with the following relationship:

log 10 kill=$K$×Flux×Residence time×$Z$/OD×Tube Diameter wherein Flux indicates the amount of UV radiation incident on the passage containing the fluid flow in the irradiation area immediately inside the passage wall, in mW cm$^{-2}$, wherein OD is the Optical Density of the fluid at the wavelength in the region where substantial virus inactivation takes place;

K is an empirically derived constant;

Tube Diameter is the internal diameter, d, of the vessel in the irradiation area, in cms; and $$Z=u(\rho/\mu)/Re^m$$

wherein u is fluid flow velocity in cm/sec, $\rho$ is fluid density in kg/m3, $\mu$ is fluid viscosity in cp, Re is the Reynolds number of the fluid whose value is defined by the formula Re=du$\rho$/$\mu$ where d, u, $\rho$ and $\mu$ have the same meaning as before, and m is a characteristic of the static mixer system, and wherein said method includes the steps of experimentally determining the value m, whereby substantially the whole of the fluid may be exposed to a similar micro-organism inactivating level of UV-irradiation whilst minimizing damage to the desired component(s) of the fluid.

12. A method of UV-irradiation of a fluid which method comprises:
   a) providing a UV-irradiation apparatus with a flow supply means set to provide a fluid flow rate in the range from a minimum flow rate to a maximum flow rate according to claim 11; and
   b) passing the fluid through said apparatus and irradiating the fluid within the apparatus with UV-radiation.

13. An apparatus suitable for use in the UV-irradiation of a biological fluid containing a desired component and a contaminating micro-organism, and which fluid has a fluid density $\rho$ in kg/m$^3$, a fluid viscosity $\mu$ in cp, a Reynolds number Re under the fluid flow conditions in the apparatus and whose value is defined by the formula Re=du$\rho/\mu$ where $\rho$ and $\mu$ have the same meaning as before, d is the internal diameter of a tube through which the fluid flow passes, and u is the velocity of the fluid flow through said tube, in use of the apparatus, and which apparatus comprises a longitudinally extending tubular vessel having wall means of a UV-transparent material disposable, in use of the apparatus, in close proximity to a UV radiation source providing UV radiation at a predetermined, micro-organism inactivating wavelength, at a predetermined Flux, where Flux is the amount of UV radiation incident immediately inside the tubular vessel wall, in mW cm$^{-2}$, within an irradiation zone, said tubular vessel having an inlet and an outlet and a passage means formed and arranged so as to define a flow path extending therebetween which is substantially free of substantial discontinuities so as to avoid substantially turbulence in fluid flowing therealong in use of the apparatus, and said passage means having a static flow mixing means with at least 20 mixer elements for repeatedly subjecting the fluid flow to a mixing operation comprising dividing and re-mixing of the fluid flow, in use of the apparatus, which static flow mixing means extends along said flow path along at least said irradiation zone, said tubular vessel having an internal diameter, d, in cms of at least 0.4, and said apparatus including fluid flow supply formed and arranged for passing fluid through said vessel, in use of the apparatus, at a fluid flow rate not less than a minimum flow rate corresponding to a maximum fluid residence time, within said irradiation area, required for efficient mixing as indicated by the maintenance of a substantially close relation between actual log kill and log kill as predicted by the below indicated relationship, with increasing residence time which obtains above said minimum flow rate and at a fluid flow rate not greater than a maximum fluid flow rate corresponding to a minimum residence time in said irradiation area required for effective inactivation of a said contaminating micro-organism by providing a desired log kill of said micro-organism, and not greater than that at which significant degradation of said desired component occurs, wherein said minimum residence time in said irradiation area is defined in accordance with the following relationship:

$$\log_{10} \text{kill} = K \times \text{Flux} \times \text{Residence time} \times Z/\text{OD} \times d$$

wherein Flux and d have the same meaning as before;
K is an empirically derived constant; and $$Z = u(\rho/\mu)/Re^m$$

wherein u, $\rho$, $\mu$ and Re have the same meaning as before, and m is a characteristic of the static mixer system whose value is determinable experimentally, whereby in use of the apparatus substantially the whole of the fluid may be exposed to a similar micro-organism inactivating level of UV-irradiation whilst minimizing damage to the desired component(s) of the fluid.

14. The apparatus according to claim 13, wherein said static flow mixing means has from 50 to 500 mixer elements.

15. The apparatus according to claim 13, wherein said vessel has an internal diameter, d, of at least 0.6 cm.

16. The apparatus according to claim 15, wherein said vessel has an internal diameter, d, of at least 1 cm.

17. The apparatus according to claim 13, wherein said vessel wall means is a material which is substantially transparent to UV across the wavelength range from 220 to 280 nm.

18. The apparatus according to claim 13, wherein the irradiation area length is from 100 to 1000% of the minimum effective irradiation area length.

19. The apparatus according to claim 18, wherein the irradiation area length is from 150 to 700% of the minimum effective irradiation area length.

20. The apparatus according to claim 13, wherein the fluid flow supply means comprises a pump means.

21. The apparatus according to claim 13, wherein the fluid flow supply means is provided with an adjustable flow rate control means adjustable in use of the apparatus for providing a desired fluid flow rate.

22. The apparatus according to claim 13, wherein said fluid flow supply means is formed and arranged for providing a flow rate corresponding to a fluid residence time within the range from 1 to 100 seconds in use of the apparatus.

23. The apparatus according to claim 22, wherein said fluid residence time is within the range from 2 to 16 seconds.

* * * * *

UNITED STATES PATENT AND TRADEMARK OFFICE
CERTIFICATE OF CORRECTION

PATENT NO. : 6,586,172 B1
DATED : July 1, 2003
INVENTOR(S) : Andrew Gunn et al.

It is certified that error appears in the above-identified patent and that said Letters Patent is hereby corrected as shown below:

<u>Title page,</u>
Item [73], Assignee, should read as follows:
-- Iatros Limited (GB) and Common Services (GB) --.

Signed and Sealed this

Thirtieth Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,586,172 B1
DATED : July 1, 2003
INVENTOR(S) : Andrew Gunn et al.

It is certified that error appears in the above-identified patent and that said Letters Patent is hereby corrected as shown below:

<u>Title page,</u>
Item [73], Assignee, should read
-- Iatros Limited (GB) and Common Services Agency (GB) --

Signed and Sealed this

Twenty-fourth Day of May, 2005

JON W. DUDAS
*Director of the United States Patent and Trademark Office*